(12) United States Patent
Lischinsky

(10) Patent No.: US 10,729,904 B2
(45) Date of Patent: Aug. 4, 2020

(54) METHODS AND DEVICES FOR TREATING ERECTILE DYSFUNCTION

(71) Applicant: OHH-MED MEDICAL LTD., Ramat-Yshay (IL)

(72) Inventor: Daniel Lischinsky, Ramat Ishay (IL)

(73) Assignee: OHH-MED MEDICAL LTD., Ramat-Yshay (IL)

( * ) Notice: Subject to any disclaimer, the term of this patent is extended or adjusted under 35 U.S.C. 154(b) by 229 days.

(21) Appl. No.: 15/878,423

(22) Filed: Jan. 24, 2018

(65) Prior Publication Data

US 2018/0147411 A1 May 31, 2018

Related U.S. Application Data

(63) Continuation of application No. 15/618,751, filed on Jun. 9, 2017, now Pat. No. 9,913,981.
(Continued)

(51) Int. Cl.
*A61N 1/36* (2006.01)
*A61N 1/06* (2006.01)
(Continued)

(52) U.S. Cl.
CPC ...... *A61N 1/36007* (2013.01); *A61B 17/2251* (2013.01); *A61F 5/41* (2013.01);
(Continued)

(58) Field of Classification Search
CPC ......... A61N 1/36007; A61N 1/36; A61F 5/41; A61B 17/2251
See application file for complete search history.

(56) References Cited

U.S. PATENT DOCUMENTS

| 6,033,398 A | 3/2000 | Farley et al. |
| 2001/0000261 A1 | 4/2001 | Redano |

(Continued)

FOREIGN PATENT DOCUMENTS

| KR | 200452897 | 3/2011 |
| KR | 20160072832 | 6/2016 |

OTHER PUBLICATIONS

International Search Report and Written Opinion of PCT Application No. PCT/IL2017/050925, dated Dec. 21, 2017.
(Continued)

*Primary Examiner* — Rex R Holmes
(74) *Attorney, Agent, or Firm* — Pearl Cohen Zedek Latzer Baratz LLP

(57) ABSTRACT

Methods and devices for treating erectile dysfunction are disclosed. Methods are aimed at reducing blood outflow from penile tissue by delivering energy to specific penile tissue that controls blood outflow from the penile tissue and causing remodeling of the specific penile tissue. Devices may be configured to generate RF energy and to apply the generated RF energy to a penis to thereby elevate a temperature of internal penile tissue above a predetermined temperature value while maintaining a penile surface below a predetermined temperature threshold. The predetermined temperature value may be set to initiate synthesis and/or a regeneration of collagen fibers in a collagen-rich penile connective tissue and/or to increase oxygenation of endothelial cells, initiate angiogenesis and neovascularization in a vascular penile tissue. Additionally, electrical penile stimulation is disclosed, possibly applicable in conjuncture with the erectile dysfunction treatment.

21 Claims, 20 Drawing Sheets

Related U.S. Application Data

(60) Provisional application No. 62/383,415, filed on Sep. 3, 2016.

(51) Int. Cl.
  *A61B 17/225* (2006.01)
  *A61F 5/41* (2006.01)
  *A61N 1/04* (2006.01)
  *A61N 1/05* (2006.01)

(52) U.S. Cl.
  CPC ............... *A61N 1/06* (2013.01); *A61N 1/36* (2013.01); *A61N 1/0452* (2013.01); *A61N 1/0476* (2013.01); *A61N 1/0521* (2013.01); *A61N 1/36034* (2017.08)

(56) References Cited

U.S. PATENT DOCUMENTS

2015/0032195 A1   1/2015  Lin et al.
2017/0215950 A1*  8/2017  Gross ............... A61B 18/1492

OTHER PUBLICATIONS

U.S. Office Action for U.S. Appl. No. 15/618,751, dated Oct. 4, 2017.

* cited by examiner

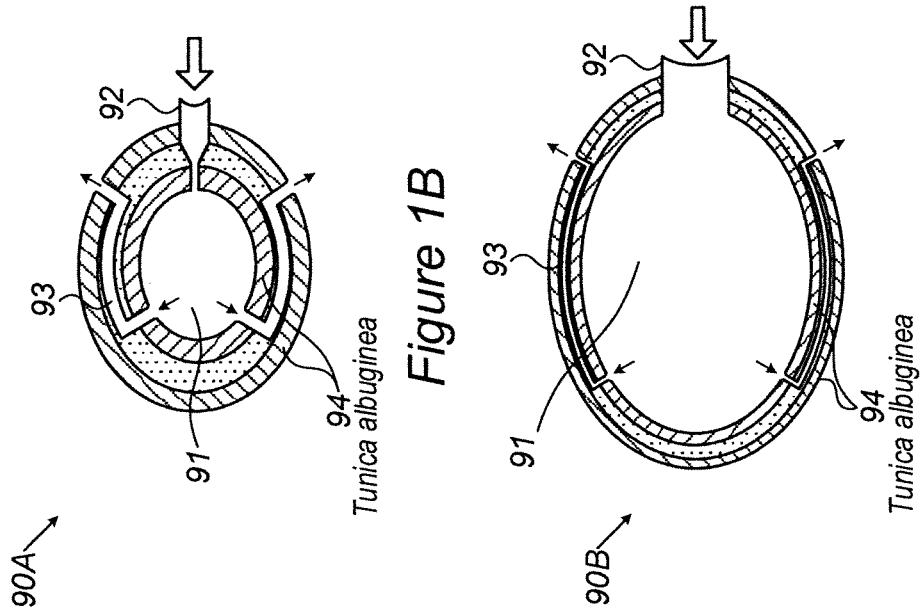
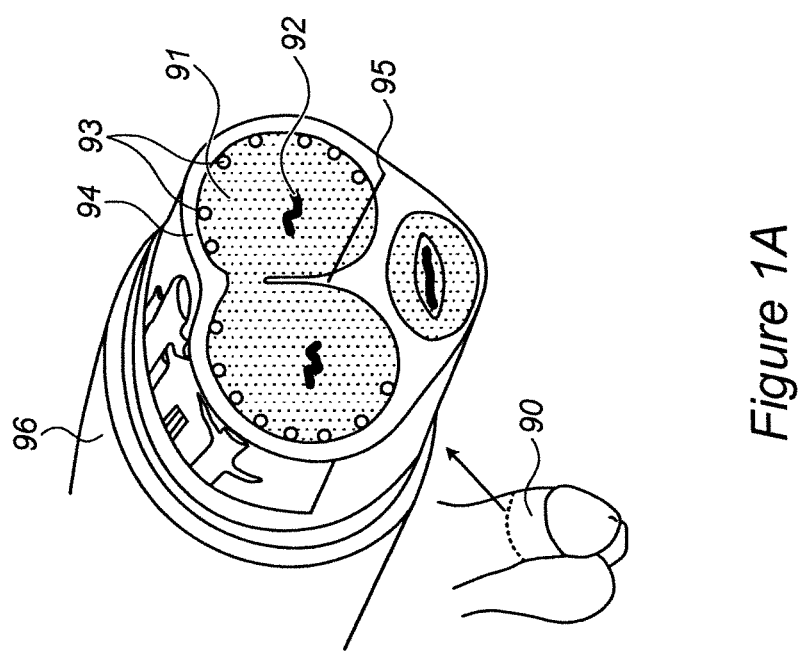

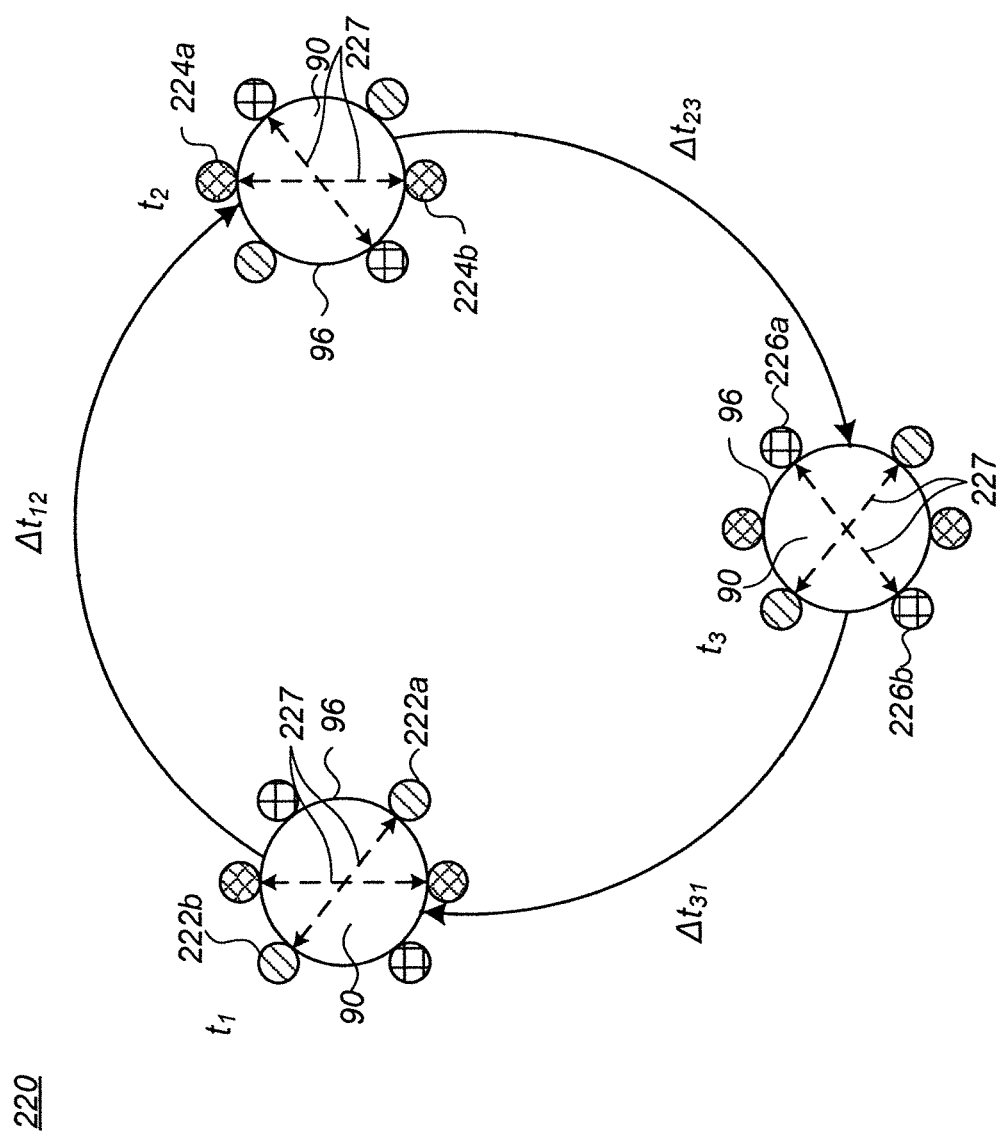

500

```
┌─────────────────────────────────────────────────────────┐
│ Delivering radiofrequency (RF) energy to inner penile   │
│ tissues of a penis of a patient via plurality of RF     │──510
│ electrode pairs contacting a penile surface             │
└─────────────────────────────────────────────────────────┘
                            ↓
┌─────────────────────────────────────────────────────────┐
│ Arranging the RF electrodes along a circumference of    │
│ the penis such that each RF electrode in each of the    │
│ RF electrode pairs of the plurality of RF electrode     │──520
│ pairs is positioned at a substantially opposite side    │
│ of the penis to provide an opposite RF electrodes       │
│ arrangement                                             │
└─────────────────────────────────────────────────────────┘
                            ↓
┌─────────────────────────────────────────────────────────┐
│ Arranging the RF electrodes along a circumference of    │
│ the penis such that RF electrodes in each RF electrode  │
│ pair of the plurality of RF electrode pairs are         │──522
│ positioned adjacent to each other to provide adjacent   │
│ RF electrodes arrangement                               │
└─────────────────────────────────────────────────────────┘
                            ↓
┌─────────────────────────────────────────────────────────┐
│ Arranging the RF electrodes in multiple sets of RF      │
│ electrode pairs, wherein the RF electrodes in each of   │
│ the sets of RF electrode pairs are arranged along a     │──523
│ circumference of the penis and wherein each of the      │
│ sets of RF electrode pairs is positioned at different   │
│ predetermined location along the penis                  │
└─────────────────────────────────────────────────────────┘
                            ↓
┌─────────────────────────────────────────────────────────┐
│ Coupling RF electrodes from different sets of RF        │
│ electrodes pairs to provide coupled RF electrode pairs, │
│ wherein the RF electrodes in each of the coupled RF     │──524
│ electrode pairs are positioned at opposite portions of  │
│ the penis with respect to each other to provide the     │
│ opposite RF electrodes arrangement                      │
└─────────────────────────────────────────────────────────┘
                            ↓
┌─────────────────────────────────────────────────────────┐
│ Coupling RF electrodes from different sets of RF        │
│ electrodes pairs to provide coupled RF electrode pairs, │
│ wherein the RF electrodes in each of the coupled RF     │──525
│ electrode pairs are positioned at the same portion of   │
│ the penis to provide the adjacent RF electrodes         │
│ arrangement                                             │
└─────────────────────────────────────────────────────────┘
                            ↓
```

*Figure 6*

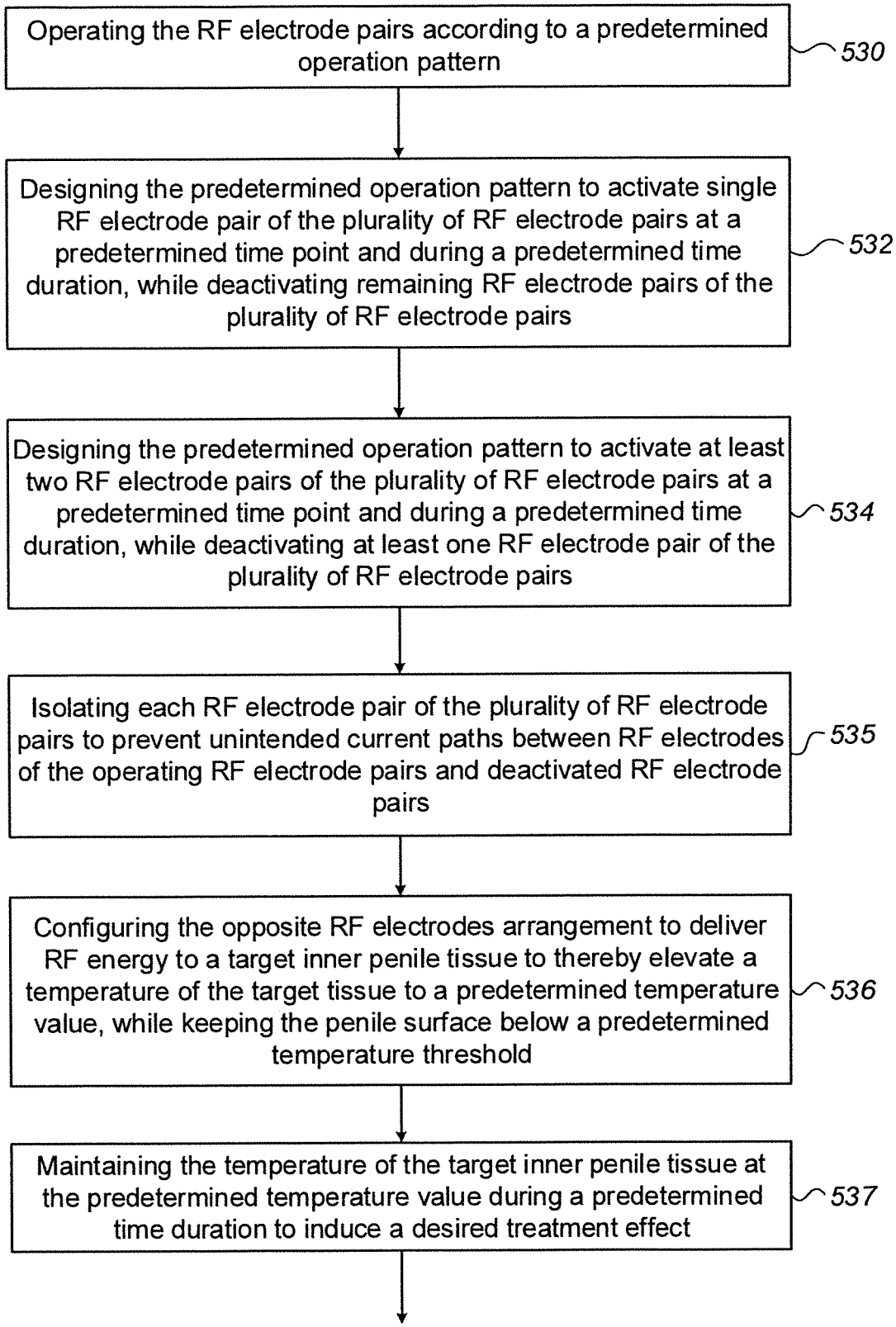
Figure 6 (cont. 1)

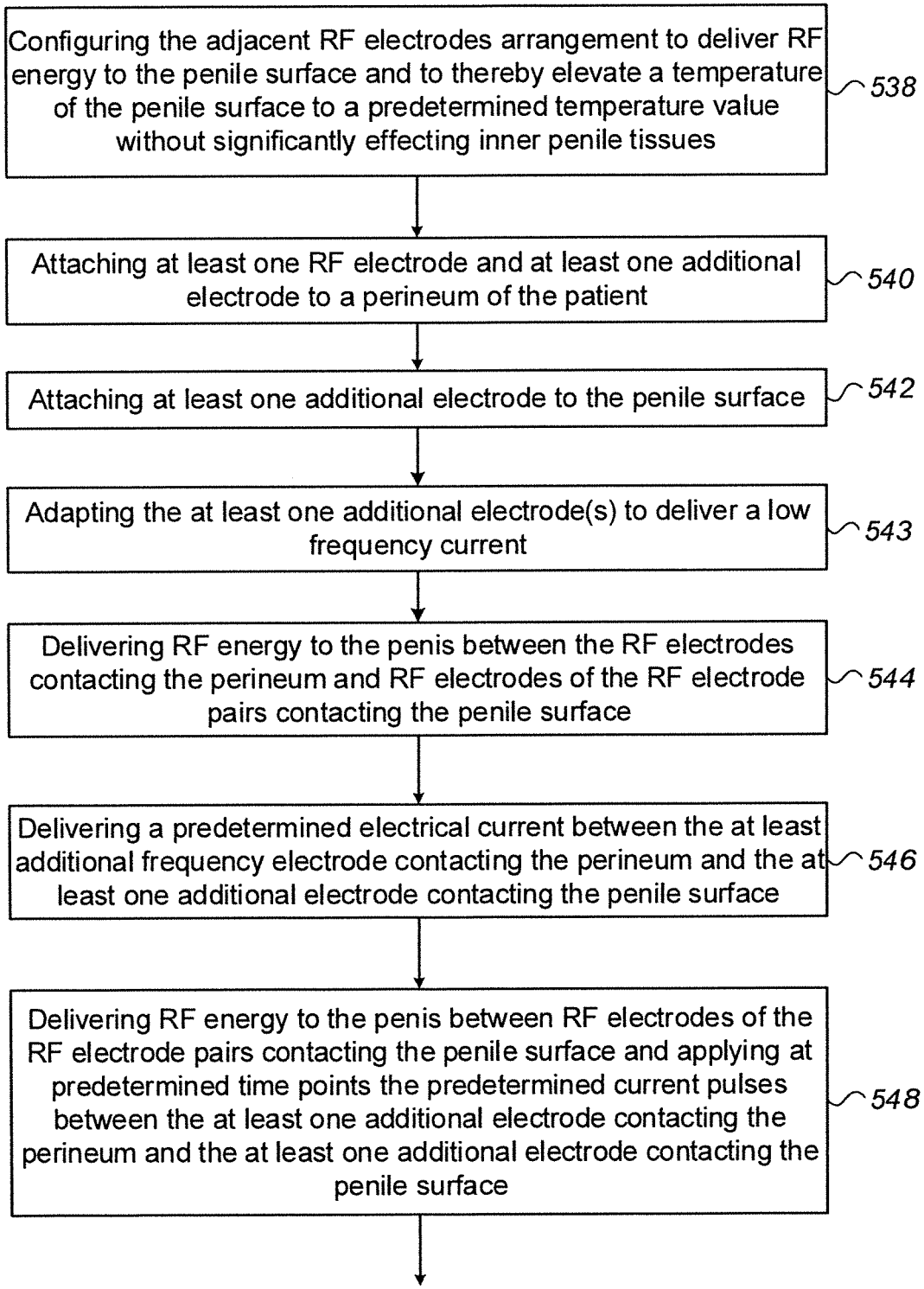
Figure 6 (cont. 2)

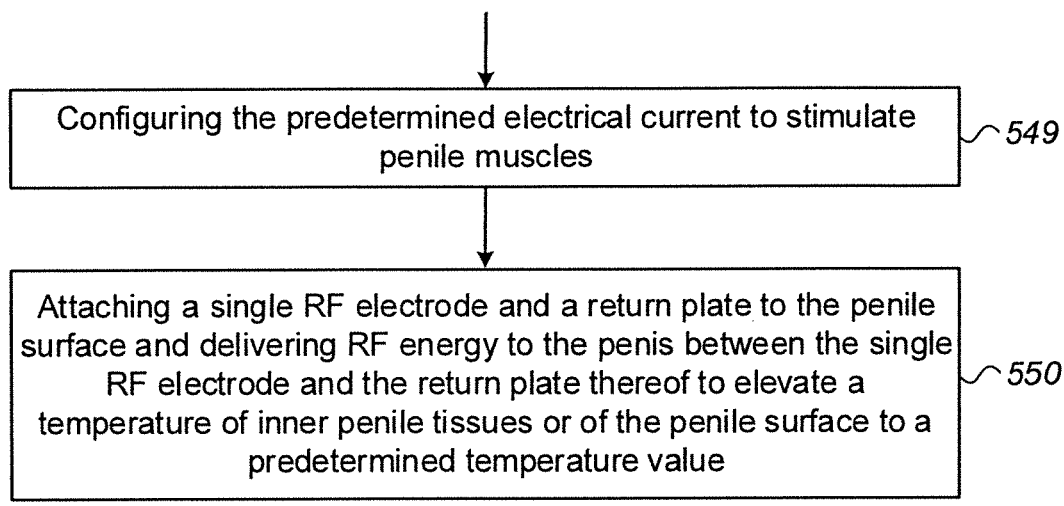
Figure 6 (cont. 3)

METHODS AND DEVICES FOR TREATING ERECTILE DYSFUNCTION

CROSS REFERENCE TO RELATED APPLICATIONS

This application is a continuation of U.S. patent application Ser. No. 15/618,751, filed on Jun. 9, 2017, now U.S. Pat. No. 9,913,981, which claims the benefit to U.S. Provisional Patent Application No. 62/383,415 filed on Sep. 3, 2016, all of which are incorporated herein by reference in their entirety.

BACKGROUND OF THE INVENTION

1. Technical Field

The present invention relates to the field of methods of treating erectile dysfunction, and more particularly, to collagen remodeling based methods of treating erectile dysfunction.

2. Discussion of Related Art

Erectile dysfunction, which may be a persistent inability to achieve and/or maintain an erection sufficient for satisfactory sexual performance, may be an age-associated disorder and may have a prevalence rate of at least 39% and 67% among 40 years old and 70 years old men, respectively. Current treatment methods of erectile dysfunction typically include medications (e.g., oral medications such as Viagra®), intra cavernosal injection therapy, vacuum constriction devices, and/or penile implants. Medications and/or vacuum constriction devices may provide a temporary improvement of sexual functioning (e.g., on-demand treatment, where the sexual act depends on the use of the treatment before the act thereof), but fail to improve or cure erectile dysfunction. Moreover, medications may have contra-indications (e.g., hypotension, nitrate medications, pulmonary veno-occlusive disease, etc.), side effects (e.g., back pain, muscular pain, headache, flushing, tinted vision, dyspepsia etc.) and/or a non-response rate (e.g., about 25%). Penile implants may serve as a solution for a patient being non-responsive to therapeutic modalities (e.g., medications), however, it is an invasive procedure associated with temporary pain and/or with risks of infection, erosion, mechanical failure and other complications.

SUMMARY OF THE INVENTION

The following is a simplified summary providing an initial understanding of the invention. The summary does not necessarily identify key elements nor limits the scope of the invention, but merely serves as an introduction to the following description.

One aspect of the present invention provides a method of treating erectile dysfunction (ED), the method comprising delivering energy to a penile tissue comprising collagen fibers, wherein the delivered energy is configured to initiate synthesis of collagen fibers in the tissue thereof.

Another aspect of the present invention provides a device for erectile dysfunction treatment, the device comprising: at least one radiofrequency (RF) generator configured to generate RF energy; a plurality of RF electrode pairs, each RF electrode in each RF electrodes pair of the plurality of RF electrode pairs configured to contact a target penile surface and connected to at least one RF generator of the at least one RF generator; a control circuitry connected to each RF electrode in each RF electrodes pair of the plurality of RF electrode pairs and connected to at least one RF generator, the control circuitry configured to switch among RF electrode pairs of the plurality of RF electrode pairs to apply the generated RF energy to the penis to thereby elevate a temperature of internal penile tissue above a predetermined temperature value while maintaining a penile surface below a predetermined temperature threshold.

Another aspect of the present invention provides a kit comprising a device for erectile dysfunction treatment and an erectile body stimulation (EBS) pad, wherein the device for erectile dysfunction is configured to generate RF energy and to apply the generated RF energy to the penis to thereby elevate a temperature of internal penile tissue above a predetermined temperature value while maintaining a penile surface below a predetermined temperature threshold, and wherein the EBS pad is configured to stimulate penile smooth muscles.

Another aspect of the present invention provides a method of erectile dysfunction treatment, the method comprising delivering radiofrequency (RF) energy to inner penile tissues of a penis of a patient via a plurality of RF electrode pairs contacting a penile surface.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 1A is a high level schematic illustration of a penis anatomy and FIGS. 1B and 1C are high level schematic illustrations of a penile erection process;

FIG. 3B-3E are high level schematic illustrations of various arrangements of RF electrode pairs of a device for erectile dysfunction treatment with respect to a penis and operational mode thereof, according to some embodiments of the invention;

FIG. 6 is a high level schematic flowchart of a method of erectile dysfunction treatment, according to some embodiments of the invention.

DETAILED DESCRIPTION OF THE INVENTION

Figure 2:
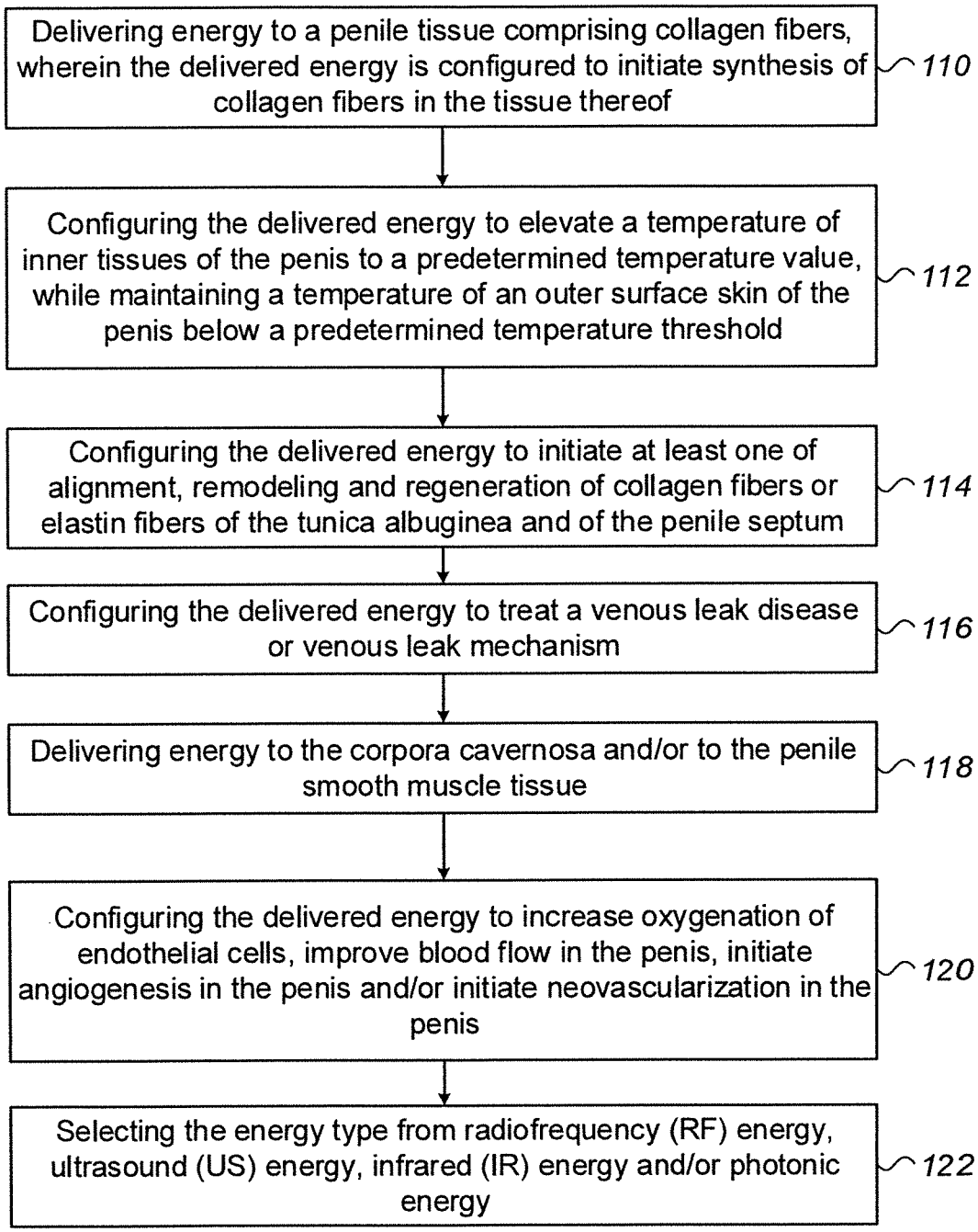
FIG. 2 is a high level schematic flowchart of a method of treating erectile dysfunction, according to some embodiments of the invention.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Methods and devices for treating erectile dysfunction are disclosed. Methods are aimed at reducing blood outflow from penile tissue by delivering energy to specific penile tissue that controls blood outflow from the penile tissue and causing remodeling of the specific penile tissue. Methods may be further aimed to maintaining and/or enhancing erectile function of a patient, and/or to preventing an erectile dysfunction. Devices may be configured to generate RF energy and to apply the generated RF energy to a penis to thereby elevate a temperature of internal penile tissue above a predetermined temperature value while maintaining a penile surface below a predetermined temperature threshold. The predetermined temperature value may be set to initiate synthesis and/or a regeneration of collagen fibers in penile tissue comprising the collagen and/or to increase oxygenation of endothelial cells, initiate angiogenesis and neovascularization in a vascular penile tissue. Additionally, electrical penile stimulation is disclosed, possibly applicable in conjuncture with the erectile dysfunction treatment. Advantageously, disclosed embodiments provide curative methods and devices for erectile dysfunction disease that may be achieved by painless and non-invasive procedures.

FIG. 1A is a high level schematic illustration of a penis 90 anatomy and FIGS. 1B and 1C are high level schematic illustrations of a penile erection process. Illustrations 90A and 90B in FIGS. 1B and 1C, respectively, indicate a flaccid state and an erect state of tunica albuginea 94 of penis 90, respectively. See e.g., Miller 2000, "Diagnostic Evaluation of Erectile Dysfunction", American Family Physician, 61(1):95-104—for more details on the physiology and illustrations clarifying erectile function.

A penile erection may be achieved due to, for example, stimulation of a penis 90 by a nervous system (e.g., due to local mechanical stimulus of penis 90 and/or due to emotional stimulus). Stimulation of penis 90 by the nervous system may lead to secretion of nitric oxide (NO) that may cause, for example, relaxation of smooth muscles of corpora cavernosa 91, which is an inner spongy erectile tissue of penis 90 (e.g., as shown in FIG. 1A). Relaxation of the smooth muscles may enable increased blood flow to corpora cavernosa 91 through arteries 92 (e.g., cavernosal arteries). As a result, corpora cavernosa 91 may expand, for example in length and in diameter (e.g., as shown in FIG. 1C, with respect to FIG. 1B), to receive at least 90% of blood involved in the penile erection.

Blood may leave corpora cavernosa 91 through veins 93 (e.g., deep dorsal veins) arranged along an outside surface of corpora cavernosa 91 (e.g., as shown in FIG. 1A). Penile erection may be maintained due to, for example, a veno-occlusive mechanism (VOM), during which expanded corpora cavernosa 91 may press veins 93 against tunica albuginea 94 (which is a fibrous envelope of corpora cavernosa 91 consisting of about 95% collagen fibers and of about 5% elastin fibers) to constrict veins 93 and thereby preventing (or substantially preventing) blood from leaving corpora cavernosa 91 and maintaining penis 90 in an erect state erection (e.g., as shown in FIG. 1C). Accordingly, tunica albuginea 94 may be directly involved in maintaining the penile erection and poor collagen fibers and/or elastin fibers expression within tunica albuginea 94 may lead, for example, to failure of the VOM and thereby to reduced erection and/or reduced rigidity of penis 90.

FIG. 2 is a high level schematic flowchart of a method 100 of treating erectile dysfunction, according to some embodiments of the invention.

Method 100 may comprise delivering (stage 110) energy to collagen-rich penile connective tissue (e.g., tunica albuginea 94 and/or a penile septum 95), wherein the delivered energy may be configured to initiate synthesis of collagen fibers in the collagen-rich penile connective tissue.

Method 100 may comprise configuring (stage 112) the delivered energy to elevate a temperature of inner tissues of the penis (e.g., of tunica albuginea 94 and/or of penile septum 95) to a predetermined temperature value, while maintaining a temperature of an outer surface skin of the penis (e.g., skin 96) below a predetermined temperature threshold.

Method 100 may comprise configuring (stage 114) the delivered energy to initiate at least one of alignment, remodeling and regeneration of collagen fibers and/or elastin fibers of tunica albuginea 94 and/or of penile septum 95. For example, application of energy having predetermined energy parameters and/or according to predetermined operation patterns (e.g., as described below with respect to FIGS. 3A-3E) may elevate a temperature of target inner tissue (or tissues) of penis 90 (e.g., tunica albuginea 93 and/or penile septum 95) to a predetermined temperature value. The predetermined temperature value may be set to induce, for example, a desired treatment effect in the target inner tissue of penis 90. For example, exposing tunica albuginea 94 and/or penile septum 95 (e.g., as shown in FIG. 1A) to temperature ranging between 42-52° C. may induce regeneration and/or remodeling of collagen fibers in these tissues.

Method 100 may comprise configuring (stage 116) the delivered energy to treat a venous leak disease or venous leak mechanism. For example, delivering energy to tunica albuginea 94 and/or penile septum 95 may, for example, induce synthesis, remodeling and/or regeneration of collagen fibers or elastin fibers in these tissues (e.g., as described above) and improve thereby the VOM which is responsible for preventing the venous leak disease or venous leak mechanism during erection (e.g., as described above with respect to FIGS. 1A-1C).

Method 100 may comprise delivering (stage 118) energy to at least one of corpora cavernosa 91 (e.g., as shown in FIG. 1A) and penile smooth muscle tissue (not shown). Method 100 may comprise configuring (stage 120) the delivered energy to increase the oxygenation of endothelial cells (e.g., within corpora cavernosa 91 and/or within the penile smooth muscle tissue) to improve blood flow in penis 90, initiate angiogenesis in penis 90 and/or initiate neovascularization in the penis. For example, exposing corpora cavernosa 91 and/or penile smooth muscle to temperature ranging between 42-52° C. may increase oxygenation of endothelial cells and initiate angiogenesis and neovascularization in these tissues.

Method 100 may comprise selecting (stage 122) energy type from a group consisting, for example, of radiofrequency (RF) electromagnetic energy, ultrasound (US) energy, infrared (IR) energy and/or photonic energy.

The inventor thus suggests a new mechanism for treating erectile dysfunction. Contrary, or possibly complementarily to prior art medical treatment which is directed at increasing the input of blood into penile tissue (e.g., by administration of sildenafil derivatives), disclosed method 100 reduces or possibly temporarily blocks the output of blood from penile tissue as a mechanism for treating erectile dysfunction. Alternatively or complementarily, disclosed method 100 may be used as a preventive treatment to delay appearance of erectile dysfunction syndromes (e.g., prophylaxis), to prevent development of erectile dysfunction disease and/or to maintain normal erectile function. Alternatively or complementarily, disclosed method 100 induces re-modeling of penile tissue to enhance or improve the organic blood output mechanisms such as vein constriction which maintain erection, and therefore may provide a long lasting effect, possibly even in the absence of additional treatment. Initial experiments indicate that method 100 actually induces an increase in common assessment tests for measuring of erectile function, such as the IIEF (international index of erectile function, see e.g., Miller 2000 cited above) which suggests a real, long-lasting improvement in the state of the patient. Method 100 may be implemented by a device 200 disclosed below, or by any equivalent apparatus which implements at least some of the stages of method 100.

Figure 3A:
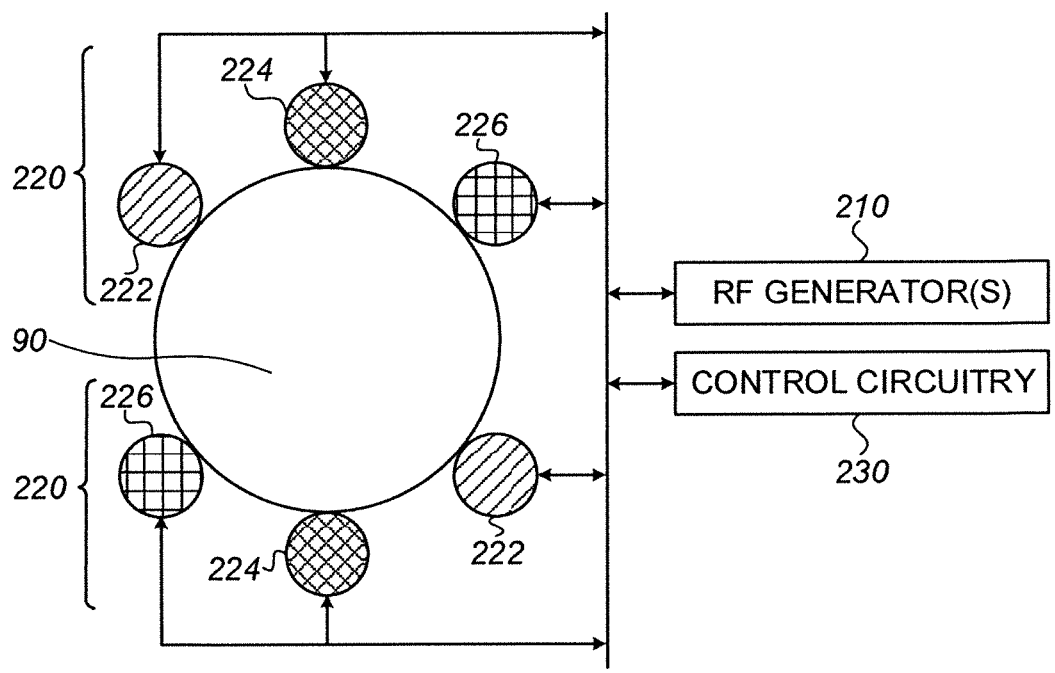
FIG. 3A is a high level schematic block diagram of a device for an erectile dysfunction treatment, according to some embodiments of the invention.

FIG. 3A is a high level schematic block diagram of a device 200 for an erectile dysfunction treatment, according to some embodiments of the invention. Device 200 is a non-limiting example for an RF-based implementation of method 100, using RF energy to reduce blood output by obstruction or constriction of veins 93 by possibly tissue re-modelling of the tunica albuginea 94 to treat erectile dysfunction.

Device 200 may comprise at least one radiofrequency (RF) generator 210 configured to generate RF energy. Device 200 may comprise a plurality of RF electrode pairs 220 connected to at least one RF generator 210 and adapted to contact penis 90 of a patient. For example, device 200 may comprise a first electrode pair 222, a second RF electrode pair 224 and/or a third RF electrode pair 226 (e.g., as shown in FIG. 3A). In some embodiments, each of RF electrode pairs 220 may be connected to a different RF generator 210. As may be apparent to a person of ordinary skill in the art, while FIG. 3A illustrates three RF electrode pairs 222, 224, 226 it is not meant to be limiting in any way and device 200 may comprise any number of RF electrode pairs 220.

In some embodiments, RF generator(s) 210 may be configured to generate RF energy at a frequency ranging between 100 KHz-40 MHz. In some embodiments, RF generator(s) 210 may be configured to generate RF energy at power ranging between 1-100 W. In some embodiments, RF generator(s) 210 may be configured to generate RF energy at power ranging between 15-25 W. In some embodiments, the power of RF energy generated by RF generator(s) 210 may be determined based on, for example, a geometry of the RF electrodes of RF electrode pairs 220 and/or on tissue parameters (e.g., impedance, geometry, size, etc.) of a patient undergoing the treatment.

Device 200 may comprise a control circuitry 230 connected to each RF electrode in each of RF electrode pairs 222, 224, 226 and to RF generator(s) 210. Control circuitry 230 may be configured to control generation and delivery of generated RF energy to penis 90 via RF electrode pairs 220 to elevate, for example, a temperature of a target internal penile tissue (e.g., corpora cavernosa 91, tunica albuginea 94, penile septum 95, penile smooth muscle tissue, etc., as shown in FIG. 1A) above a predetermined temperature value.

In some embodiments, control circuitry 230 may be configured to control RF generator(s) 210 to generate RF energy having predetermined energy parameters. The predetermined energy parameters may comprise, for example, at least one of a predetermined frequency, phase, intensity and/or polarity. In some embodiments, RF generator(s) 210 may be further controlled (e.g., by control circuitry 230) to perform multiplexing of predetermined energy parameters thereof to generate predetermined energy patterns. The predetermined energy patterns may comprise, for example, frequency pattern(s), phase pattern(s), intensity pattern(s), modulation pattern(s) and/or waveform pattern(s). In some embodiments, control circuitry 230 may be configured to operate RF electrode pairs 220 according to a predetermined operation pattern. The predetermined operation pattern may comprise, for example, a mode, timing and/or time duration of RF electrodes operation.

In various embodiments, at least one of the energy parameters, energy patterns, operation patterns or any combination thereof may be determined and controlled (e.g., by control circuit 230) based on a desired depth of RF energy delivery (e.g., depending on a target inner penile tissue) and/or based on a desired temperature value (e.g., depending on a desired treatment effect).

FIG. 3B-3E are high level schematic illustrations of an arrangement of RF electrode pairs 220 of a device 200 for erectile dysfunction treatment with respect to a penis 90 and operational mode of thereof, according to some embodiments of the invention.

Figure 3B:
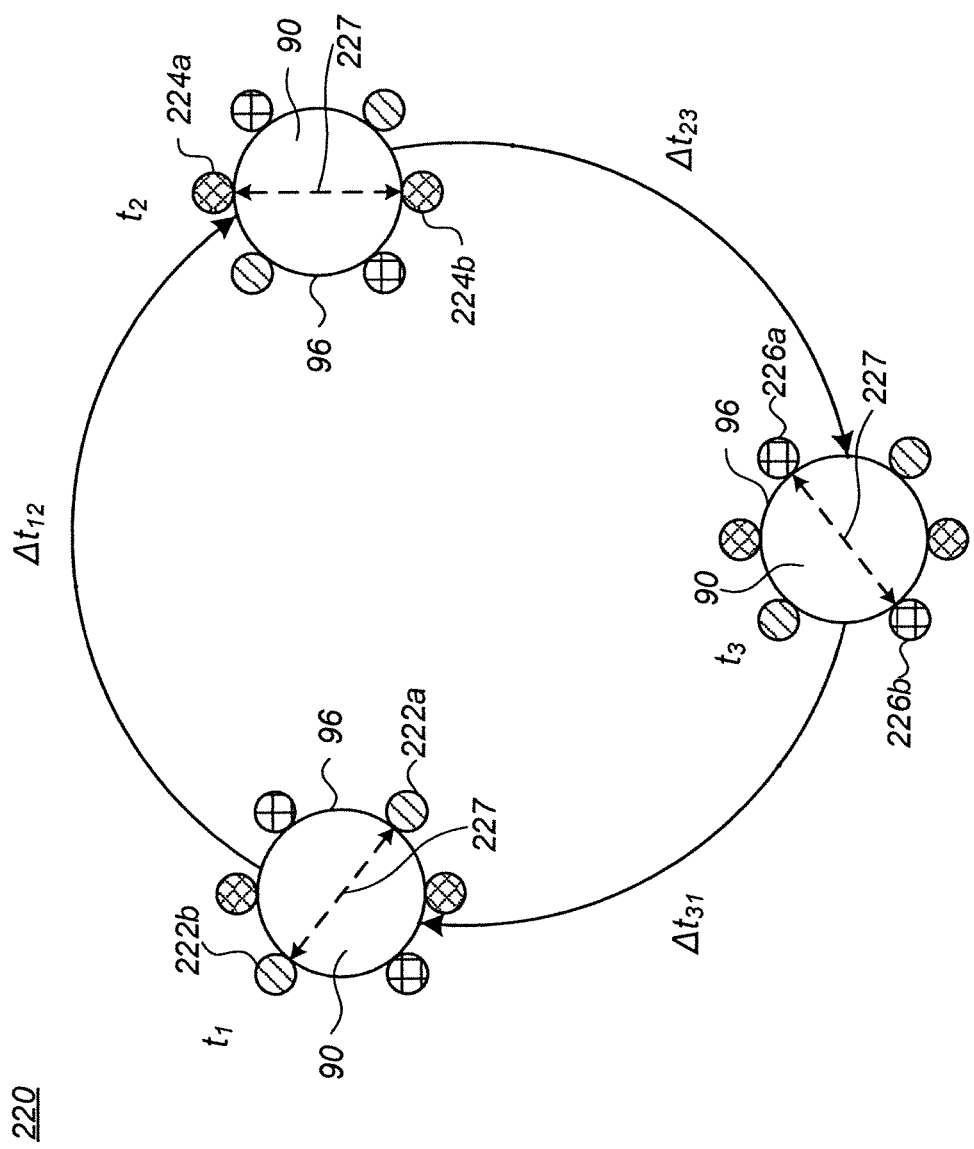

In some embodiments, RF electrode pairs 220 of device 200 may be arranged along a circumference of penis 90 such that each RF electrode in each of RF electrode pairs 222, 224 and 226 is positioned at a substantially opposite side of penis 90 (e.g., as shown in FIGS. 3A-3C). Control circuitry 230 may be configured to operate each of RF electrode pairs 220 separately (e.g., as described below with respect to FIG. 3F-3G) to drive, for example, electrical current between RF electrodes of operating RF electrode pair only and to prevent leakage of the current thereof to other RF electrodes.

Control circuitry 230 may be configured to operate RF electrode pairs 220 according to a predetermined operation pattern. The operation pattern may be predetermined to elevate a temperature of a desired inner penile tissue to a predetermined temperature value, while maintaining penile surface 96 (e.g., skin of penis 90) below a predetermined temperature threshold.

In some embodiments, the predetermined operation pattern may comprise activation of a single RF electrode pair of plurality of RF electrode pairs 220 at each time point during a treatment procedure (e.g., as shown in FIG. 3B). For example, the predetermined operation pattern may comprise activation (e.g., by control circuitry 230) of first pair of RF electrodes 222 at a first predetermined time point $t_1$ and for a first predetermined time duration $\Delta t_{12}$ (e.g., as shown in FIG. 3B). The predetermined operation pattern may further comprise deactivation (e.g., by control circuitry 230) of first RF electrode pair 222 and activation of second RF electrode pair 224 at a second predetermined time point $t_2$ (e.g., $t_2=t_1+\Delta t_{12}$) and for a second predetermined time duration $\Delta t_{23}$ (e.g., as shown in FIG. 3B). The predetermined operation pattern may further comprise deactivation (e.g., by control circuitry 230) of second RF electrode pair 224 and activation of third RF electrode pair 226 at a third predetermined time point $t_3$ (e.g., $t_3=t_2+\Delta t_{23}$) and for a third predetermined time duration $\Delta t_{31}$ (e.g., as shown in FIG. 3B).

In some embodiments, the predetermined operation pattern may comprise simultaneous activation of two (or optionally more) RF electrode pairs of plurality of RF electrode pairs 220 at each time point. For example, the predetermined operation pattern may comprise activation (e.g., by control circuitry 230) of first pair of RF electrodes 222 and second pair of RF electrodes 224 at a first predetermined time point $t_1$ such that both first RF electrode pair 222 and second RF electrode pair 224 are simultaneously operating for a first predetermined time duration $\Delta t_{12}$ (e.g., as shown in FIG. 3C). The predetermined operation pattern may further comprise deactivation (e.g., by control circuitry 230) of first RF electrode pair 222 and activation of third RF electrode pair 226 at a second predetermined time point $t_2$ (e.g., $t_2=t_1+\Delta t_{12}$) such that both second RF electrode pair 224 and third RF electrode pair 226 are simultaneously operating for a second predetermined time duration $\Delta t_{23}$ (e.g., as shown in FIG. 3C). The predetermined operation pattern may further comprise deactivation (e.g., by control circuitry 230) of second RF electrode pair 224 and activation of first RF electrode pair 222 at a third predetermined time point $t_3$ (e.g., $t_3=t_2+\Delta t_{23}$) such that both third RF electrode pair 226 and first RF electrode pair 222 are simultaneously operating for a third predetermined time duration $\Delta t_{31}$ (e.g., as shown in FIG. 3B).

In various embodiments, the predetermined operation pattern may comprise operating RF electrode pairs 220 in a predetermined order, for example in a clockwise direction (e.g., as described above with respect to FIGS. 3B-3C) or a counterclockwise direction (not shown). Alternatively or complementarily, the predetermined operation pattern may comprise random activation of RF electrode pairs 220.

Positioning RF electrodes of each of RF electrode pairs 222, 224, 226 at substantially opposite sides of penis 90 (e.g., as shown in FIGS. 3A-3C), application of each of the RF electrode pairs thereof separately and/or according to the predetermined operation pattern may drive electrical current 227 (e.g., schematically indicated by dashed arrows in FIG. 3C) via deep inner penile tissues (e.g., corpora cavernosa 91, tunica albuginea 94, etc.) thereby elevating the temperature of the inner tissues thereof and preventing overheating of penile surface 96.

In various embodiments, time durations (e.g., $\Delta t_{12}$, $\Delta t_{23}$, $\Delta t_{31}$) of RF electrode pairs 220 operation may be set to prevent elevation of penile surface 96 above a predetermined temperature threshold (e.g., in non-limiting examples, 38° C., 40° C., 42° C., possibly 44° C. or other temperature thresholds for not causing damage and/or unwanted sensations), for example by setting relatively short $\Delta t_{12}$, $\Delta t_{13}$, $\Delta t_{31}$ values (e.g., 1-2 sec as non-limiting examples) and yet elevating a temperature of a desired inner penile tissue (e.g., tunica albuginea 94 and/or penile septum 95) to a predetermined temperature value (e.g., values within the range 42-52° C., as a non-limiting example). In various embodiments, time durations of RF electrode pairs 220 operation (e.g., $\Delta t_{12}$, $\Delta t_{23}$, $\Delta t_{31}$) may be predetermined based on at least one of: contact area of RF electrodes with a tissue, power of supplied RF energy location of RF electrode pairs 220 along penis 90 and/or any combination thereof.

In some embodiments, a total treatment time may be determined based on a desired treatment effect. For example, maintaining collagen-rich penile tissue (e.g., tunica albuginea 94) for predetermined time duration ranging between 1 sec to 15 min at a temperature ranging between 42-52° C. may induce regeneration and/or remodeling of collagen fibers in these tissues. In some embodiments, higher temperature (e.g., in a 42-52° C. range) maintained for longer time (e.g., in a 1 sec-15 min range) may enhance a desired treatment effect in a tissue. In some embodiments, a minimal treatment time to achieve a desired treatment effect may be at least 30 sec.

Figure 3D:
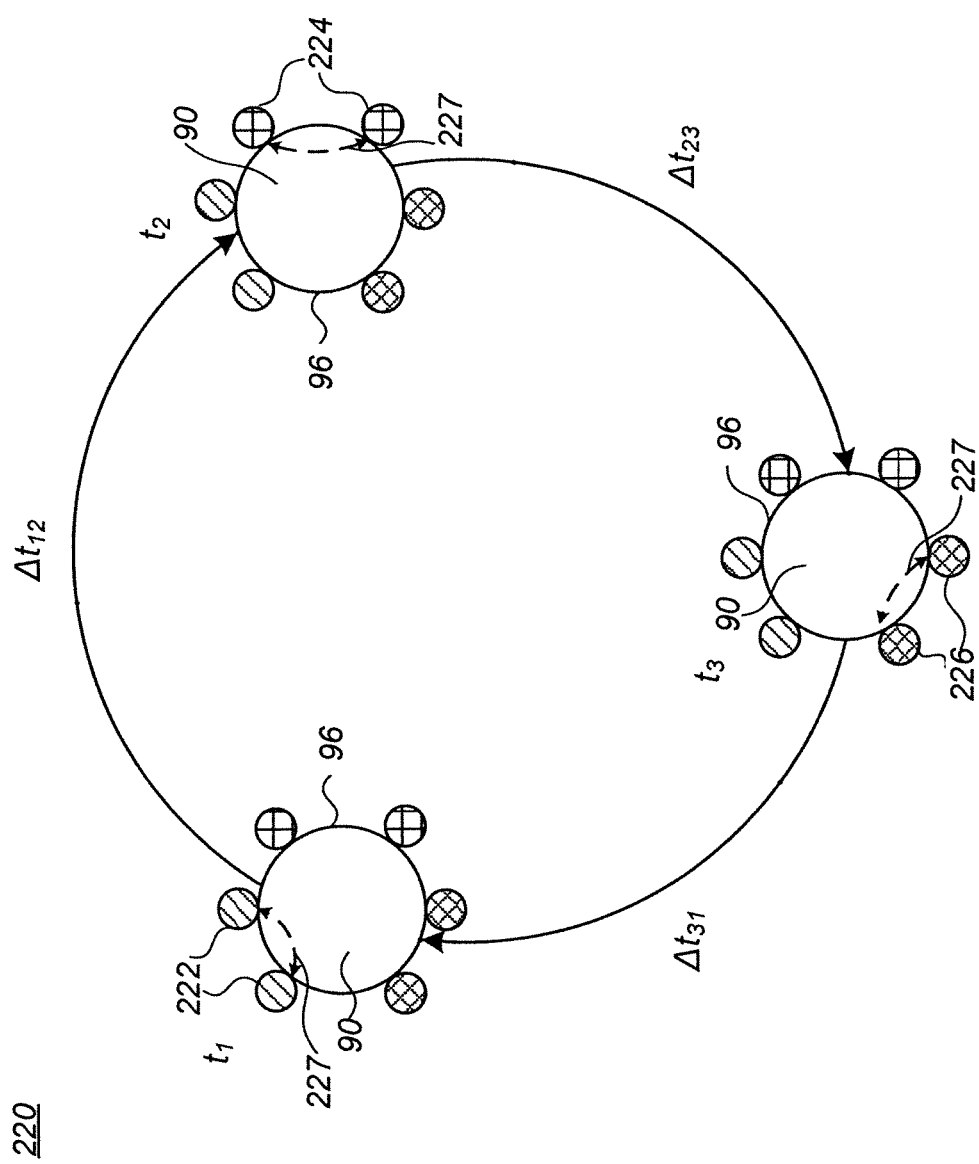
Figure 3E:
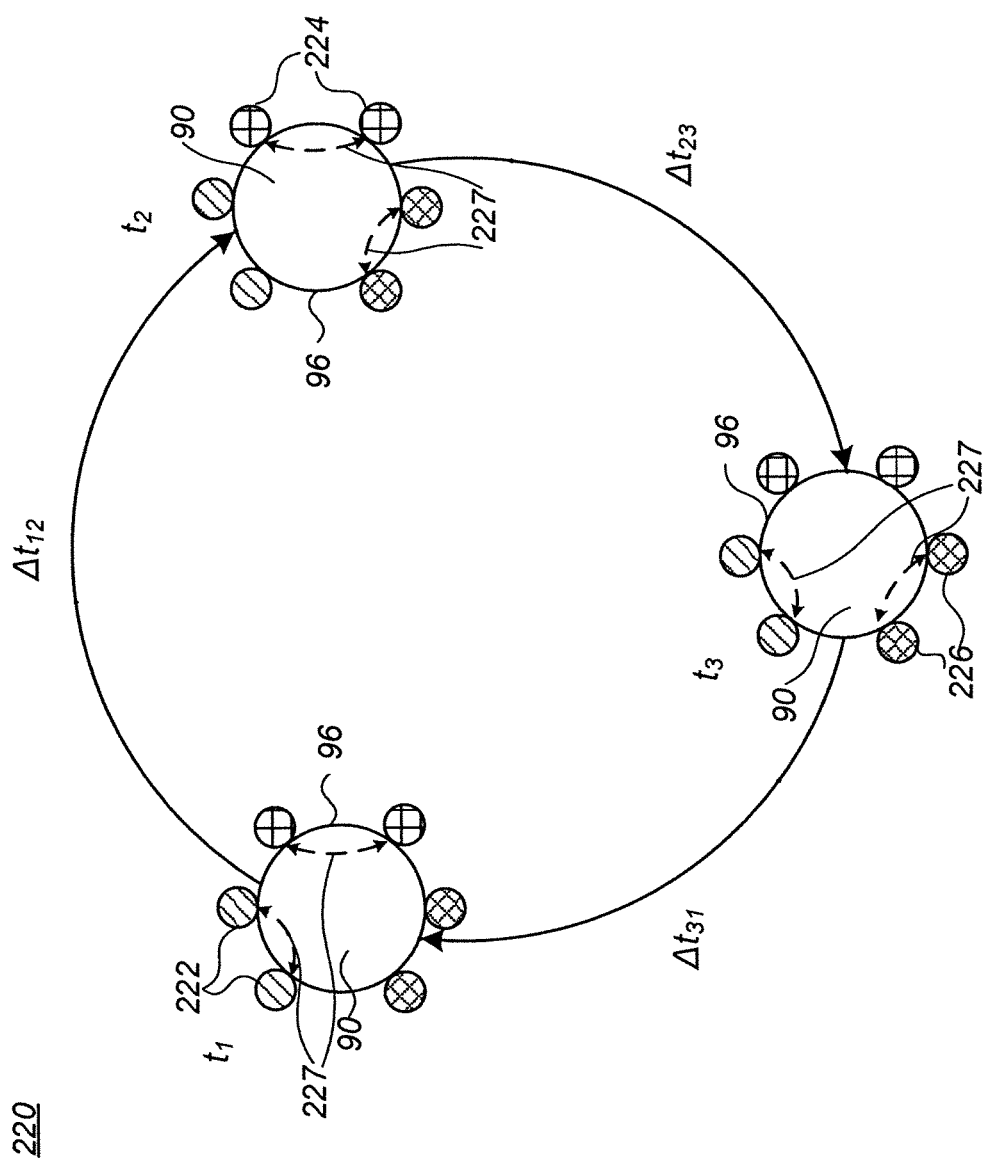

In some embodiments, RF electrode pairs 220 of device 200 may be arranged along a circumference of penis 90 such that RF electrodes in each of RF electrode pairs 222, 224 and 226 are positioned adjacent to each other (e.g., as shown in FIG. 3D). RF electrode pairs 220 in the adjacent arrangement of RF electrodes may be operated (e.g., by control circuitry 230) according to the predetermined operation pattern that may comprise, for example, activation of a single RF electrode pair of plurality of RF electrode pairs 220 or simultaneous activation of two (or optionally more) RF electrode pairs of plurality of RF electrode pairs 220 at each time point during a treatment procedure, as shown in FIG. 3D and FIG. 3E, respectively. It is noted that the disclosed adjacent arrangement of the RF electrodes may be applied to heat surface tissues without significantly affecting deeper tissues, which may be required in some embodiments of device 200.

In various embodiments, device 200 may comprise a single RF electrode and a return plate that may be connected to penile surface 96 (not shown) and may be configured to deliver RF energy to penis 90 to elevate a temperature of inner penile tissues (e.g., corpora cavernosa 91, tunica albuginea 94, penile septum 95, etc., as shown in FIG. 1A) and/or of the surface penile tissue thereof.

Figure 3F:
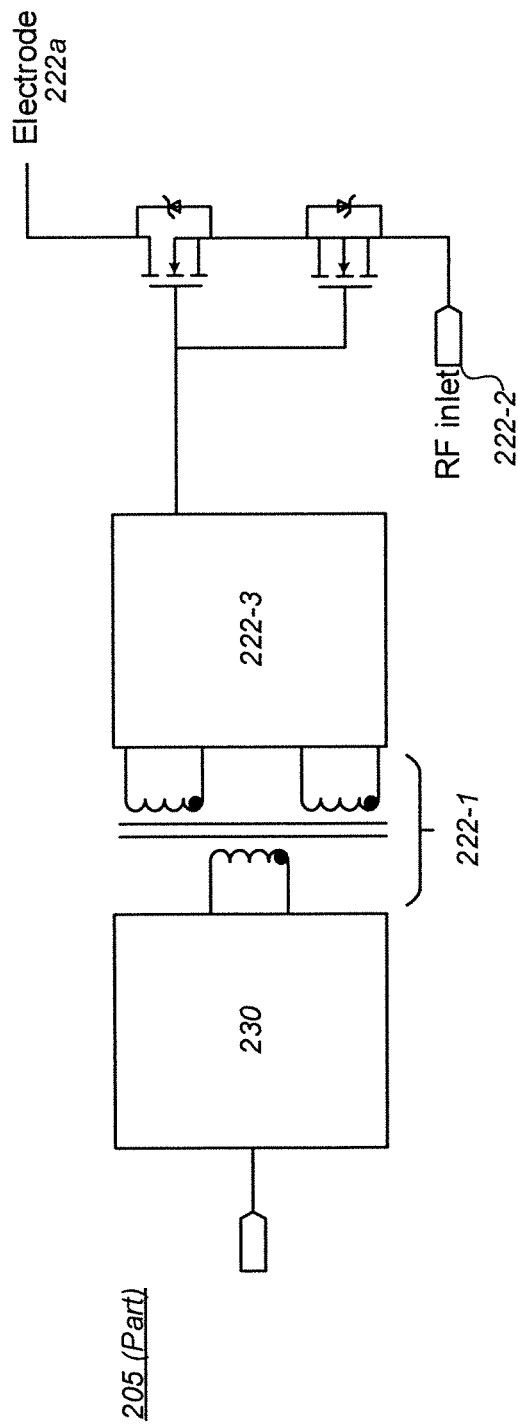
FIGS. 3F and 3G are high level schematic block diagrams of an electronic circuitry of a device for an erectile dysfunction treatment, according to some embodiments of the invention.
Figure 3G:
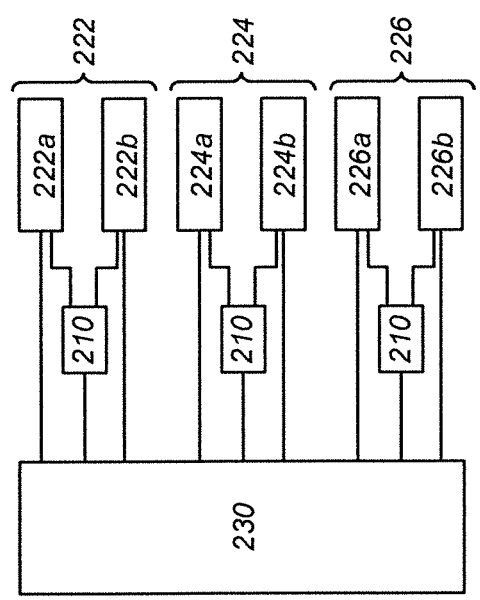

FIGS. 3F and 3G are high level schematic block diagrams of electronic circuitry 205 of a device 200 for an erectile dysfunction treatment, according to some embodiments of the invention. Electronic circuitry 205 provides a non-limiting example illustrating the isolation of RF electrode pairs from each other in the control scheme, designed to prevent unintended current paths between RF electrodes of activated and deactivated RF electrode pairs (e.g., as described above with respect to FIGS. 3B-3D) to prevent thereby overheating of skin tissue by avoiding too long accidental activation of any of the RF electrodes.

In some embodiment, each of RF electrode pairs 222, 224 and 226 may be connected to a different RF generator 210 and/or each RF electrode in each of RF electrode pairs 222, 224, 226 may be connected to a control circuitry 230 (e.g., as shown in FIG. 3G).

In some embodiments, control circuitry 230 may be configured to operate each of RF electrode pairs 220 separately and to decouple all of RF electrode pairs 220 from each other to drive, for example, electrical current between RF electrodes of operating RF electrode pair only and to prevent leakage of the current thereof to other RF electrodes. For example, during operation of first RF electrode pair 222 (e.g., during first time period $\Delta t_{12}$, as shown in FIG. 3C) each of second and third RF electrode pairs 224, 226, respectively may be decoupled from operating first RF electrode pair 222 (and optionally from the respective RF generator(s) 210). Decoupling of deactivated RF electrode pairs 224, 226 from operating first pair of RF electrodes 222 may ensure electrical current flow between RF electrodes of operating first RF electrode pair 222 and prevent incidental current leakage to at least one of RF electrodes of deactivated second and third RF electrode pairs 224, 226, respectively.

In various embodiments, each RF electrode in each of RF electrode pairs 220 may be connected to control circuitry 230 using a transformer, and/or may comprise at least one of control circuitry subunit and/or RF inlet. For example, RF electrode 222a in first RF electrode pair 222, may be coupled to control circuitry 230 of device 200 using a transformer 222-1 and/or may comprise at least one RF inlet 222-2 coupled to, for example, respective RF generator 210. RF electrode 222a may further comprise a control circuitry subunit 222-3 configured to operate in association with control circuitry 230 to, for example, activate and deactivate the RF electrode thereof, according to, for example, predetermined operation pattern.

Figure 4A:
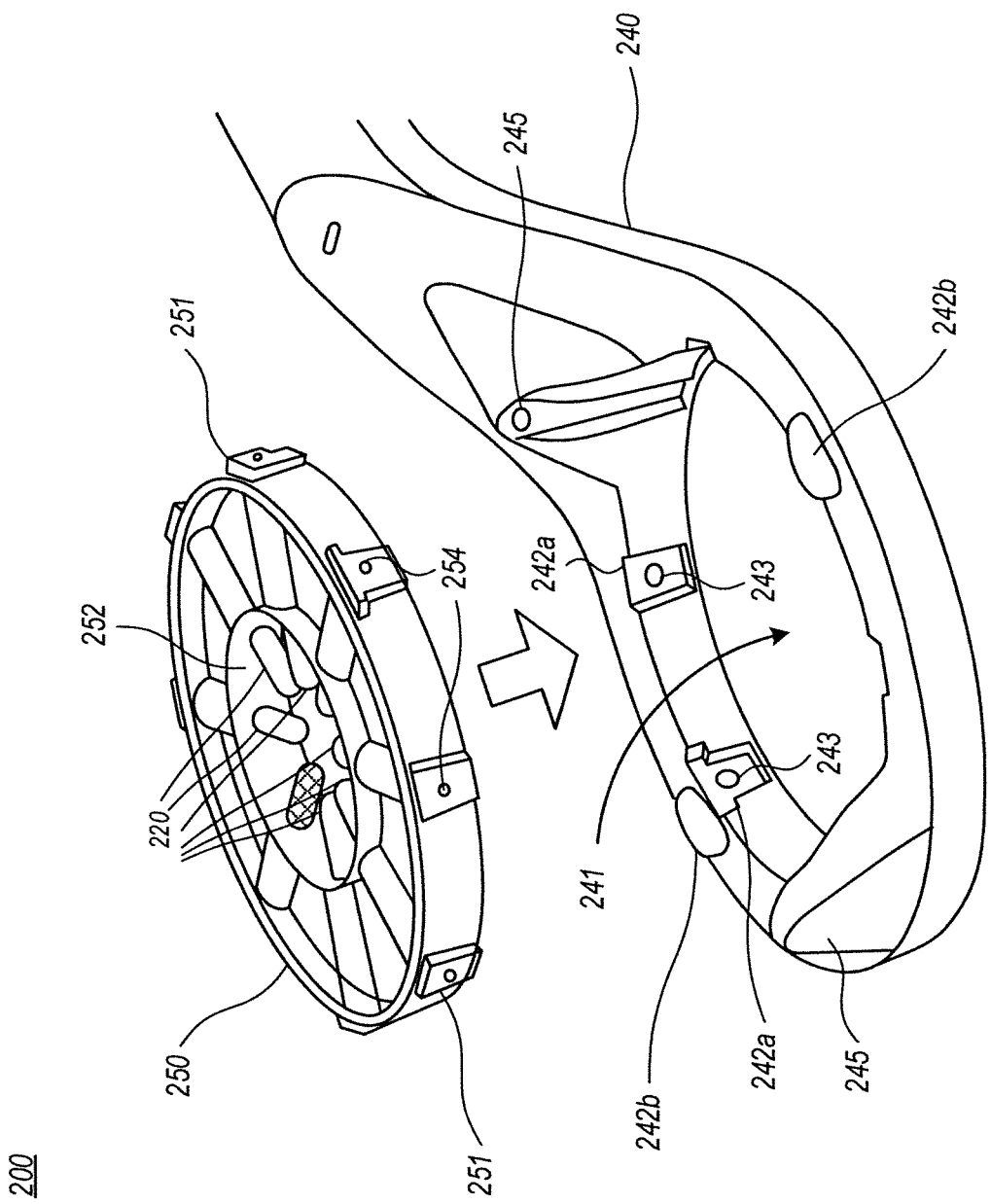
FIGS. 4A-4B are high level schematic illustrations of a device for an erectile dysfunction treatment, according to some embodiments of the invention.
Figure 4B:
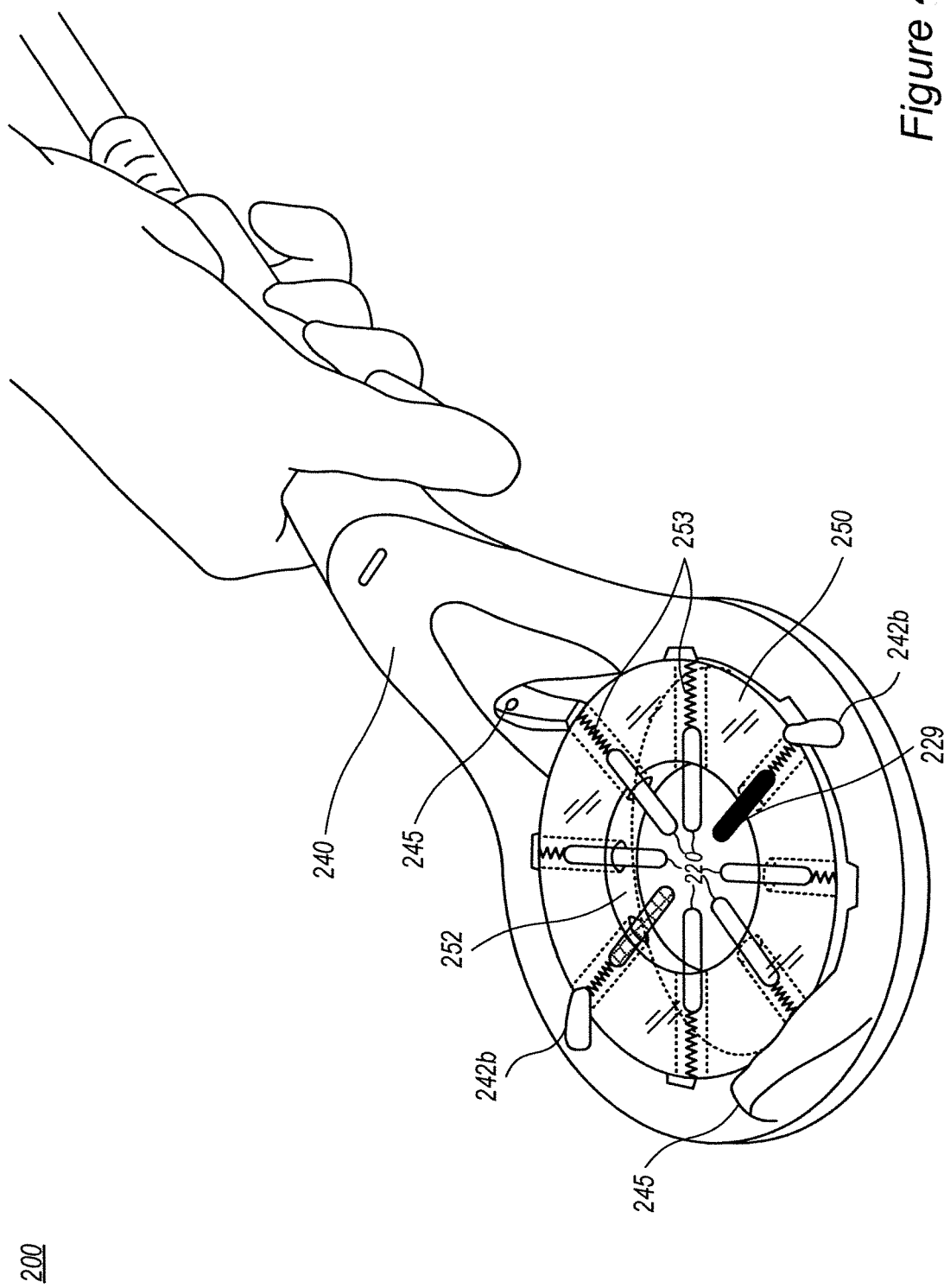

FIGS. 4A-4B are high level schematic illustrations of a device 200 for an erectile dysfunction treatment, according to some embodiments of the invention. Illustrations in FIG. 4A and in FIG. 4B illustrate disassembled and assembled sates of device 200, respectively.

Device 200 may comprise a reusable support 240 and a disposable support 250. Disposable support 250 may be adapted in shape and size to be removably connected to reusable support 240. For example, disposable support 250 may have an annular shape and reusable support 240 may comprise an annular opening 241 adapted in shape and size to accommodate disposable support 250 (e.g., as shown in FIG. 4A). In some embodiments, disposable support 250 may comprise protrusions 251 and reusable support 240 may comprise mating indents 242a and clips 242b (e.g., as shown in FIGS. 4A-4B) configured to secure the connection of reusable support during operation of device 200.

In some embodiments, reusable support 240 may be connected to control unit (not shown) comprising RF generator(s) 210 and control circuitry 230 (e.g., as described above with respect to FIGS. 3A-3G).

Disposable support 250 may comprise a central opening 252 configured to accommodate plurality of RF electrode pairs 220 (e.g., as described above with respect to FIGS. 3A-3G) and to receive penis 90 of a patient. RF electrode pairs 220 may be arranged to protrude inwards from central opening 252 and/or may be mechanically adjustable (e.g., may be spring 253 loaded, as shown in FIG. 4B) to ensure a proper contact of the RF electrodes thereof with penis 90.

The removable connection of disposable support 250 to reusable support 240 may be configured to enable delivery of the RF energy (e.g., generated by RF generators 210, as described above with respect to FIGS. 3A-3G) to each RF electrode in each of RF electrode pairs 220. For example, disposable support 250 and reusable support 240 may comprise electrically conductive caps 254 and 243, respectively, positioned at an interface between each RF electrode in each of RF electrode pairs 220 and reusable support 240 (e.g., as shown in FIG. 4A) to enable an electrical current to flow from RF generator(s) 210 to penis 90 via the RF electrodes thereof.

Figure 5A:
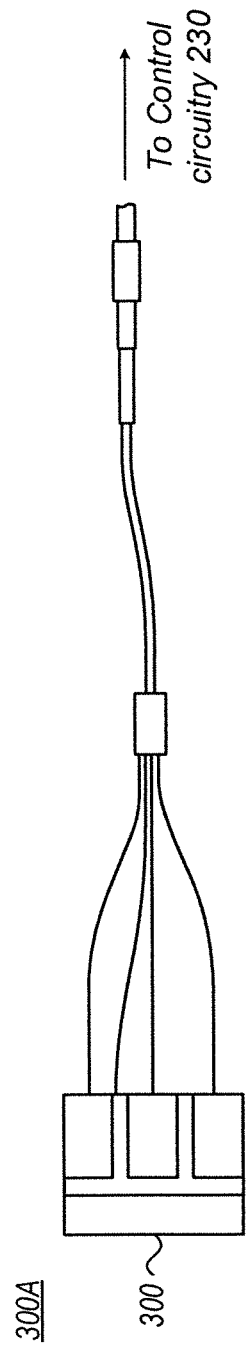
FIGS. 5A-5C are high level schematic illustrations of a pad for erectile body stimulation (EBS), according to some embodiments of the invention.
Figure 5B:
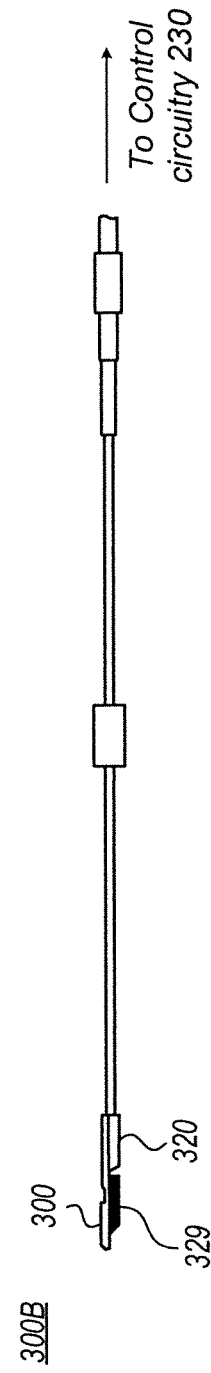
Figure 5C:
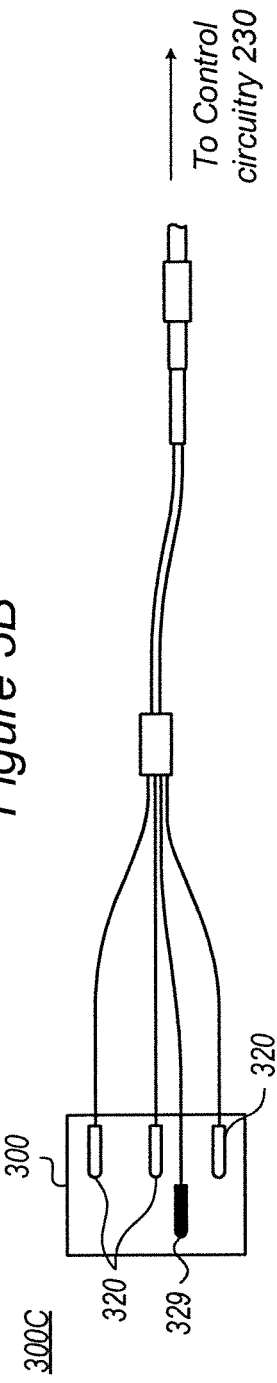
Figure 5D:
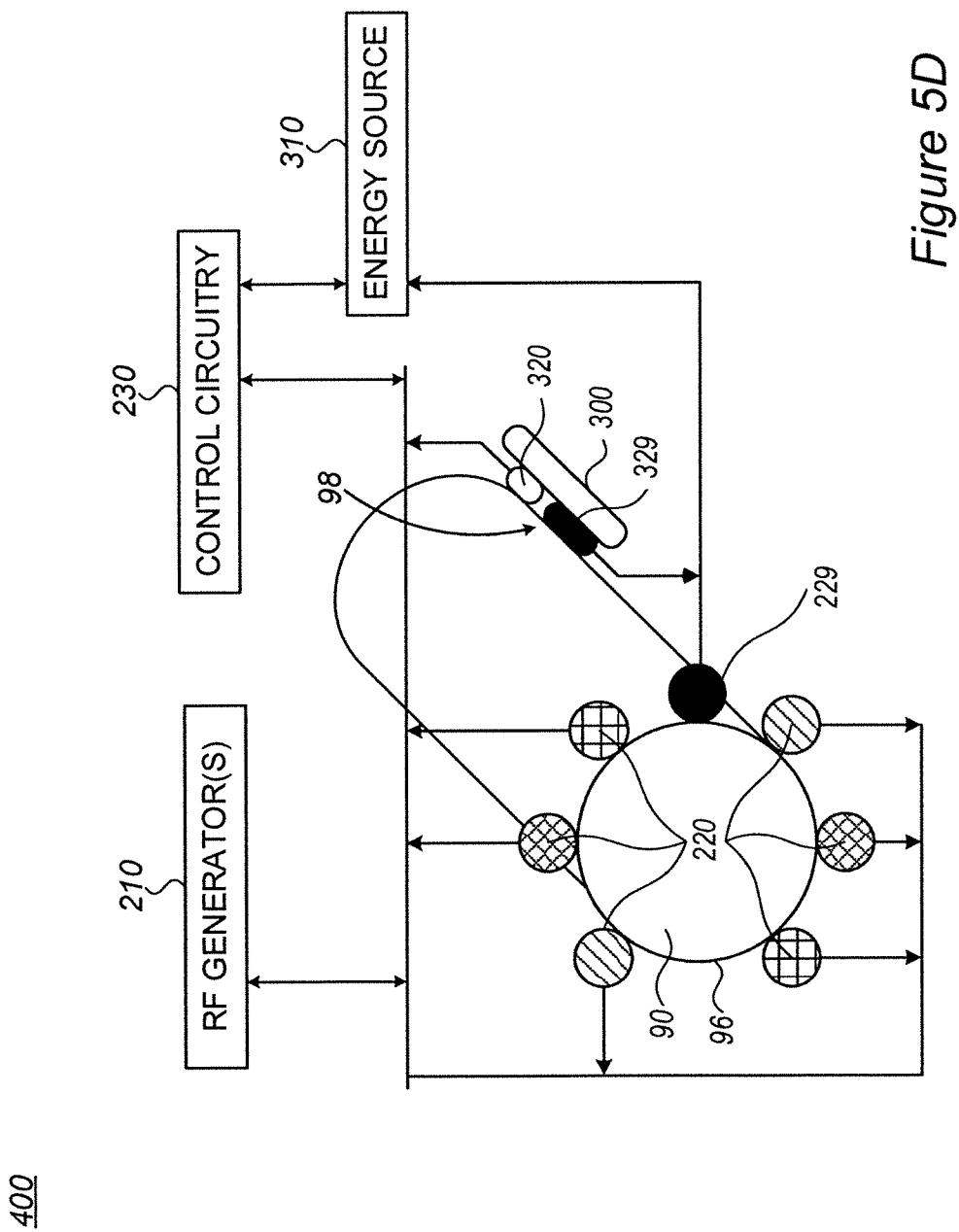
FIG. 5D is a high level schematic block diagram and FIG. 5E is a high level schematic illustration of a kit comprising a pad for erectile body stimulation (EBS) and a device for an erectile dysfunction treatment, respectively, according to some embodiments of the invention.
Figure 5E:
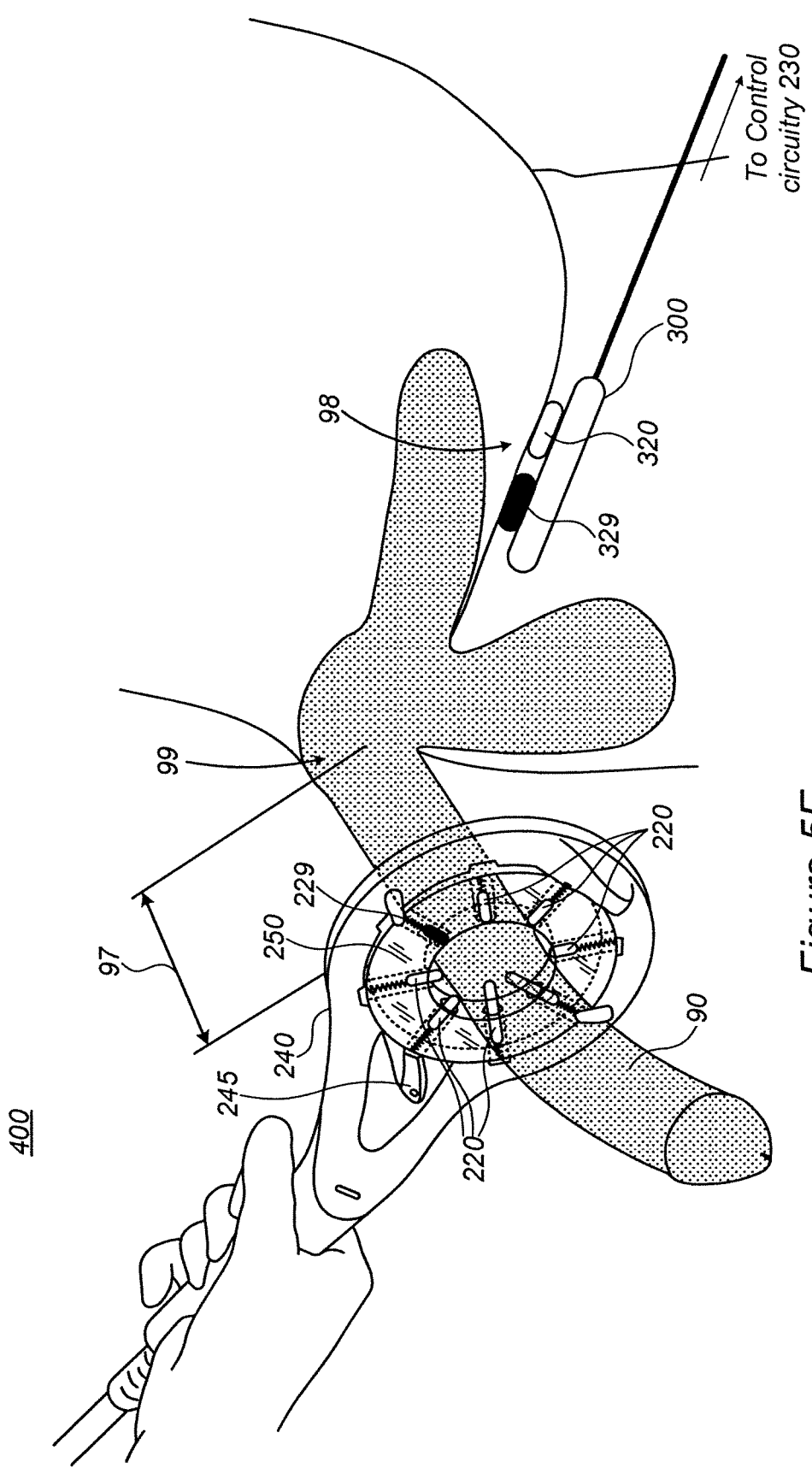

In some embodiments, device 200 may be positioned at a predetermined distance from a base of penis 90 (e.g., as shown in FIG. 5E). The distance may be predetermined based on a target treatment region of penis 90. In some embodiments, the distance may be varied during a treatment procedure to apply the treatment (e.g., to deliver RF energy) to various regions along penis 90. In various embodiments, the distance may be continuously varied (e.g., using reusable support 240) during a treatment procedure to apply the treatment to a larger region of penis 90 and/or to avoid overheating of a specific region of penis 90 above a predetermined temperature threshold.

Reusable support 240 may comprise at least one temperature sensor 245 configured to monitor a temperature of penile surface 96. In some embodiments, temperature sensor(s) 245 may be, for example an infrared (IR) thermometer. Temperature sensor(s) 245 may be connected to control circuitry 230 (not shown) and control circuitry 230 may be configured to discontinue or adapt the RF energy delivery upon detection of the penile surface 96 temperature exceeding a predetermined temperature threshold.

FIGS. 4C-4F are high level schematic illustrations of various configurations of a disposable support 250 for a device 200 for an erectile dysfunction treatment, according to some embodiments of the invention.

In some embodiments, disposable support 250 may be designed as a sleeve 250a adapted is shape and size to receive and accommodate penis 90 during a treatment procedure.

Sleeve 250a may comprise at least one set of RF electrode pairs 220. In some embodiments, RF electrodes in each of RF electrode pairs 220 may be arranged along a longitudinal axis of the sleeve (e.g., as shown in FIG. 4C). In various embodiments, control circuity 230 may be configured to operate the longitudinally arranged RF electrode pairs 220 in the opposite RF electrodes arrangement (e.g., as described above with respect to FIGS. 3B-3C) and/or in the adjacent RF electrodes arrangement (e.g., as described above with respect to FIGS. 3D-3E).

Figure 4D:
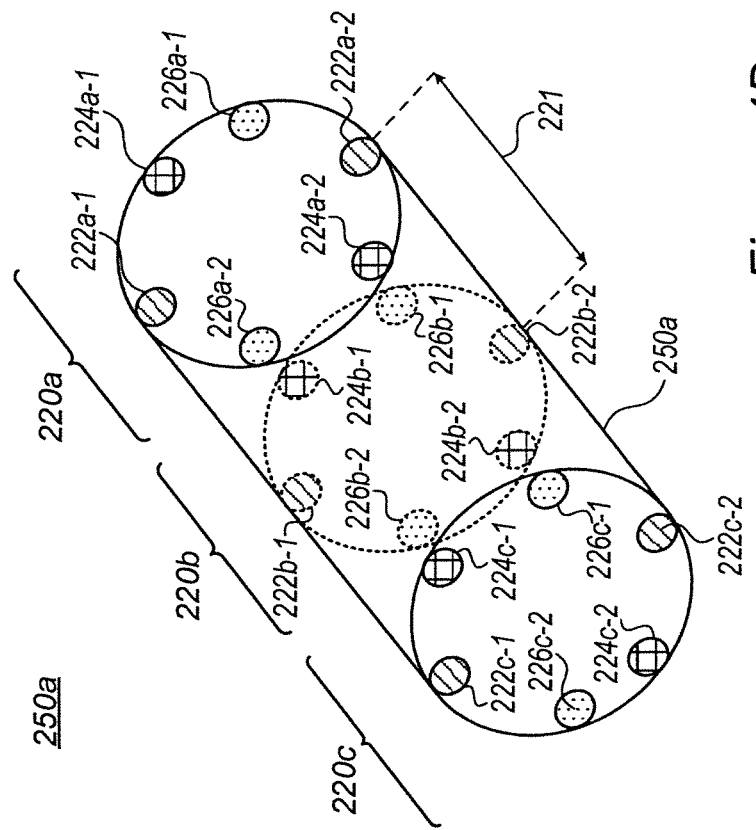
FIGS. 4C-4F are high level schematic illustrations of various configurations of a disposable support for a device for an erectile dysfunction treatment, according to some embodiments of the invention.
Figure 4C:
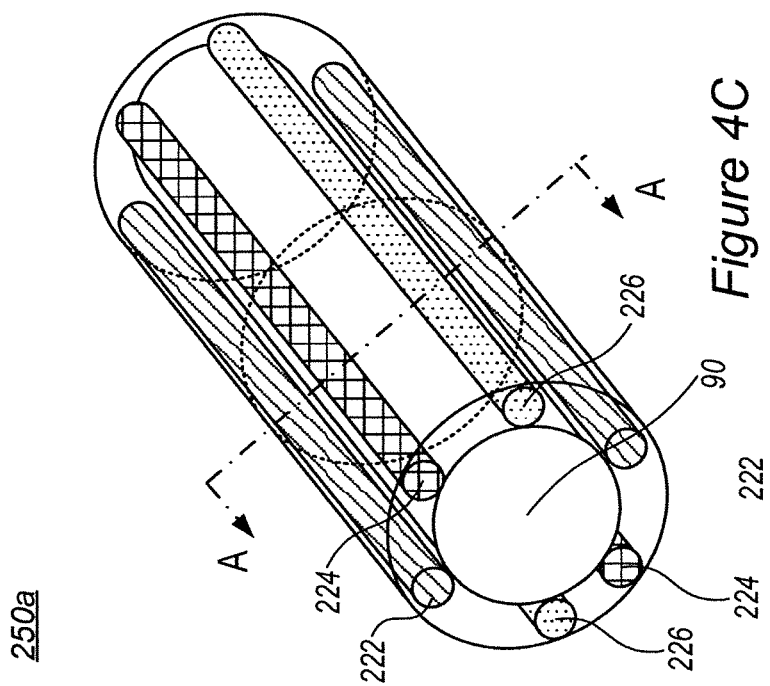

In some embodiments, sleeve 250a may comprise multiple sets of RF electrode pairs 220 positioned along a longitudinal axis of the sleeve (e.g., as shown in FIG. 4D). For example, sleeve 250a may comprise a first set 220a of RF electrode pairs, a second set 220b of RF electrode pairs and/or a third set 220c of RF electrode pairs. RF electrodes in each of sets 220a, 220b, 220c of RF electrodes may be, for example, surface electrodes. In some embodiments, the RF electrodes may be, for example embedded within sleeve 250a. Embedding of the RF electrodes within sleeve 250a may, for example, enable capacitive coupling of the RF electrodes with the RF energy delivered via the RF electrodes thereof to a target tissue. Sets 220a, 220b and 220c of RF electrode pairs may be positioned at a predetermined distance 221 from each other. Sleeve 250a may be made from a flexible and/or stretchable material (e.g., silicone) to ensure, for example, a proper contact of the RF electrodes with penis 90. As may be apparent to a person of ordinary skill in the art, while FIG. 4C illustrates three sets 220a, 220b and 220c of RF electrode pairs, it is not meant to be limiting in any way and sleeve 250a may comprise any number of sets of RF electrode pairs. In some embodiments, sleeve 250b may eliminate a need in reusable support 240 (e.g., as described above with respect to FIGS. 4A-4B).

In some embodiments, control circuity 230 of device 200 may be configured to operate each of sets 220a, 220b and 220c of RF electrode pairs in a way that ensures electrical current path between the RF electrodes of the respective set and prevents current paths between RF electrodes of different sets (e.g., as described above with respect to FIG. 3F-3G). RF electrodes in each of sets 220a, 220b and/or 220c of RF electrode pairs may be arranged and operated in the opposite RF electrodes arrangement (e.g., as described above with respect to FIGS. 3B-3C) and/or in the adjacent RF electrodes arrangement (e.g., as described above with respect to FIGS. 3D-3E). In various embodiments, control circuity 230 may be configured to operate sets 220a, 220b and 220c of RF electrode pairs in sequence (e.g., separately) or simultaneously.

Alternatively or complementarily, RF electrodes from different sets of RF electrode pairs may be coupled to deliver electrical current between the respective coupled electrodes. In various embodiments, coupled RF electrode pairs may be arranged and operated in an opposite coupled RF electrodes arrangement or in an adjacent coupled RF electrodes arrangement. In certain embodiments, sleeve 250a may be configured to support an array of electrodes 222, 224, 226 which may be controlled separately and digitally, to be operated independently of each other, while maintaining contact with the penis. The digital control of the electrodes may enable maintaining the contact of the electrodes with the penis while ensuring safety. The electrodes in the array may be operated to form electrode pairs at a specified spatio-temporal pattern, e.g., activating electrode pairs along the penis at different times to treat different regions in the penis tissue consecutively, without physically moving sleeve 250b and electrodes 222, 224, 226. In certain embodiments, electrode pairing may be carried out dynamically, to optimize the delivery of heat to internal tissue in the penis, while maintain the surface of the penis below any specified heating threshold.

For example, RF electrode 222a-1 from set 220a may be coupled with RF electrode 222b-2 from set 220b positioned at opposite portion of sleeve 250a with respect to RF electrode 222a-1, RF electrode 224a-1 from set 220a may be coupled with RF electrode 224b-2 from set 220b positioned at opposite portion of sleeve 250a with respect to RF electrode 224a-1 and/or RF electrode 226a-1 from set 220a may be coupled with RF electrode 226b-2 from set 220b positioned at opposite portion of sleeve 250a with respect to RF electrode 226a-1 to provide the opposite coupled RF electrode arrangement. Control circuitry 230 may be further configured to operate the coupled RF electrode pairs of the opposite coupled RF electrode arrangement according to a predetermined operation pattern, for example as described above with respect to FIGS. 3B-3C.

In another example, RF electrode 222a-1 from set 220a may be coupled with RF electrode 222b-1 from set 220b positioned at the same portion of sleeve 250a as RF electrode 222a-1, RF electrode 224a-1 from set 220a may be coupled with RF electrode 224b-1 from set 220b positioned at the same portion of sleeve 250a as RF electrode 224a-1 and/or RF electrode 226a-1 from set 220a may be coupled with RF electrode 2226b-1 from set 220b positioned at the same portion of sleeve 250a as RF electrode 226a-1 to provide the adjacent coupled RF electrode arrangement. Control circuitry 230 may be further configured to operate the coupled RF electrode pairs of the adjacent coupled RF electrode arrangement according to a predetermined operation pattern, for example as described above with respect to FIGS. 3D-3E.

Control circuitry 230 may be further configured to operate each of the coupled RF electrode pairs separately to drive electrical current between RF electrodes of operating coupled RF electrode pair only and to prevent leakage of the current thereof to other RF electrodes (e.g., as described above with respect to FIGS. 3F-3G).

In some embodiments, RF electrodes from adjacent sets of RF electrode pairs may be coupled (e.g., sets 220a, 220b as described above with respect to FIG. 4D). In some embodiments, RF electrodes from sets which are not adjacent to each other (e.g., sets 220a, 220c) may be coupled (not shown).

Figure 4E:
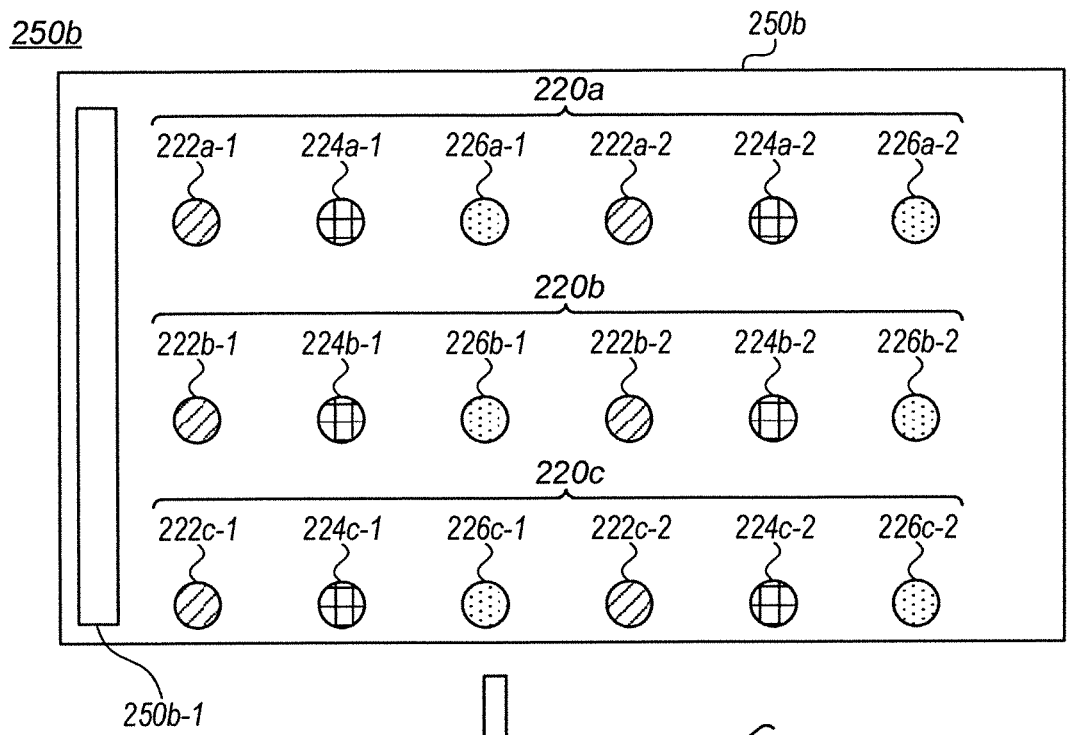
Figure 4F:
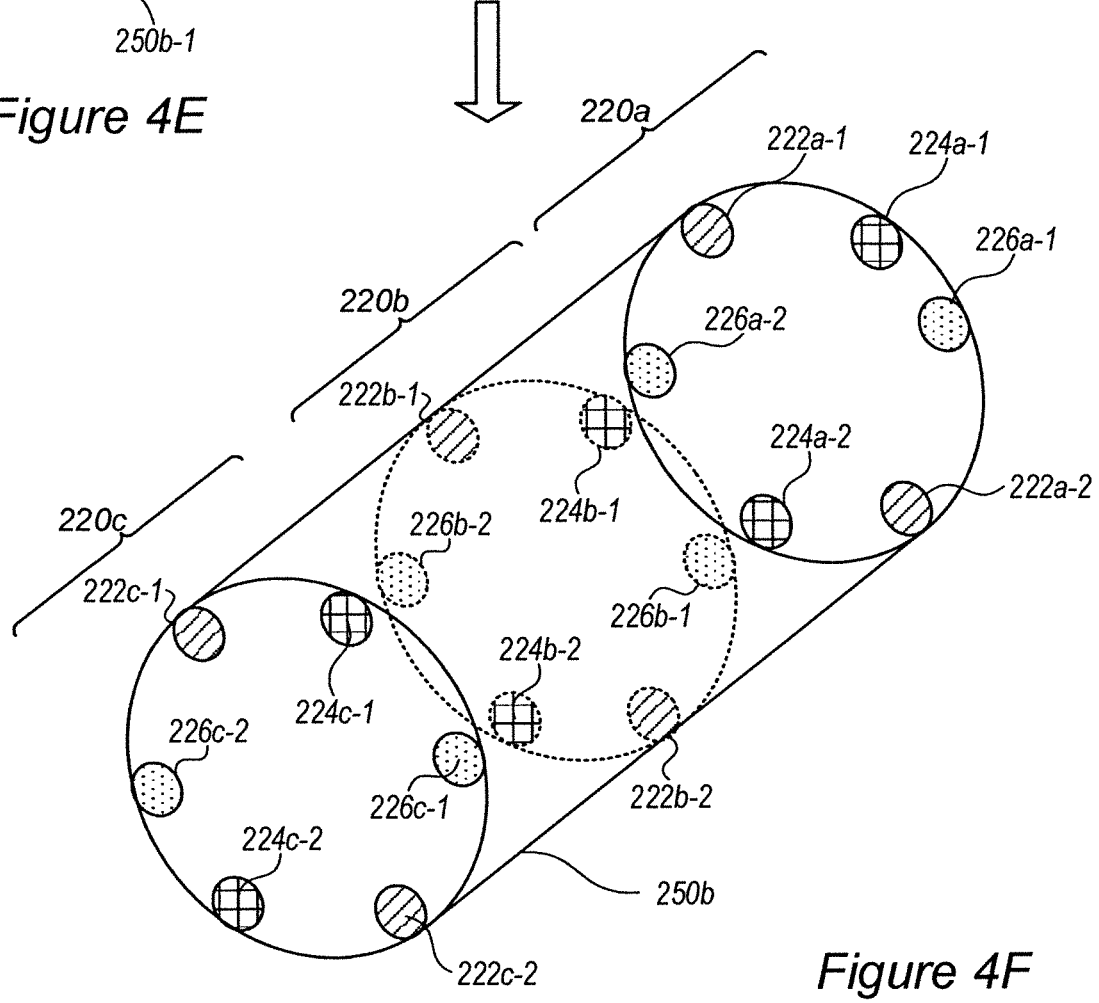

In some embodiments, disposable support 250 may be designed as an openable sleeve 250b, for example as shown in FIGS. 4E-4F. Illustrations in FIGS. 4E and 4F illustrate open and closed sates of openable sleeve 250b, respectively. Openable sleeve 250b may be made from a flexible and/or stretchable material to enable, for example, a rolling of the sleeve around penis 90 and to ensure a proper contact of the RF electrodes with penis 90. In some embodiments, openable sleeve 250b may be made of, for example, a flexible printed circuit board (PCB) that may be rolled around penis 90 and may comprise printed routings coupling the RF electrodes of sleeve 250b with at least one connector 250b-1 (e.g., located on openable sleeve 250b, as shown in FIG. 4E). In some embodiments, connector(s) 250b-1 may be configured to couple the RF electrodes of openable sleeve 250b (e.g., via the printed routing in the PCB thereof) to control circuity 230 of device 200 (not shown).

In some embodiments, disposable support 250 embodied as sleeve 250a or openable sleeve 250b which may comprise multiple sets of RF electrode pairs positioned at predetermined locations along the sleeve thereof may enable applying RF energy to various locations along penis 90 during a single treatment procedure.

In some embodiments, a fluid or a gel may be used during treatment with device 200 to reduce, for example, a friction between RF electrodes and penile surface 96, to improve electrical conductivity through penile tissue (e.g., to reduce an impedance of penile surface 96), or cool penile surface 96.

FIGS. 5A-5C are high level schematic illustrations of a pad 300 for erectile body stimulation (EBS), according to some embodiments of the invention. Illustrations 300A, 300B and 300C in FIGS. 5A, 5B and 5C, respectively represent a top view, a side view and a bottom view of pad 300, respectively. Pad 300 is further connected to control circuitry 230 and energy source 310 as illustrated in FIG. 5D.

Pad 300 may comprise at least one RF electrode 320 attached to pad's 300 surface and configured to deliver RF energy to a tissue. Pad 300 may comprise at least one electrode 329 attached to pad's 300 surface and configured to deliver predetermined electrical current to the tissue. In some embodiments, the predetermined electrical current may be, for example, low frequency current that may range, for example, between 1 Hz-900 KHz. Pad 300 may be configured to be mechanically connected to a tissue (e.g., to a perineum 98 of a patient) to ensure a proper contact of RF electrode(s) 320 and electrode(s) 329 with the tissue thereof. In various embodiments, pad 300 may be connected to a tissue using, for example, a disposable and/or reusable intermediate layer (not shown) that may be made, for example, from silicone.

FIG. 5D is a high level schematic block diagram and FIG. 5E is a high level schematic illustration of a kit 400 comprising a pad 300 for erectile body stimulation (EBS) and a device 200 for an erectile dysfunction treatment, respectively, according to some embodiments of the invention.

Kit 400 may comprise a device 200 for erectile dysfunction treatment and pad 300 for erectile body stimulation (EBS). Kit 400 may comprise an energy source 310 configured to generate and to deliver predetermined electrical current to a target tissue. In some embodiments, energy source 310 may generate, for example, low frequency electrical current that may range, for example, between 1 Hz-900 KHz. Kit 400 may comprise a control unit (not shown) configured to control the operation of pad 300 and device 200. Alternatively or complementary, control unit 230 of device 200 may be configured to control the operation of both device 200 and pad 300. In some embodiments, RF electrodes 320 of pad 300 may be connected to RF generator(s) 210 and to control circuitry 230 of device 200, and electrode 329 of pad 300 may be connected energy source 310 and to control circuitry 230 thereof (e.g., as shown in FIG. 5D).

In some embodiments, pad 300 may be used to attach RF electrodes 320 and electrode 329 to, for example, perineum 98 of a patient (e.g., as shown in FIGS. 5D-5E) while RF electrode pairs 220 of device 200 may be positioned (e.g., using reusable support 240 and disposable support 250) to contact penis 90 of the patient (e.g., as shown in FIGS. 5D-5E).

Device 200 may further comprise at least one electrode 229 embedded in disposable support 250 along with RF electrode pairs 220 (e.g., as shown in FIG. 5E). The predetermined electrical current (e.g., generated by energy source 310) may be configured to flow between electrode 329 of pad 300 and electrode 229 of device 200 thereof. In some embodiments, the predetermined electrical current (e.g., low frequency electrical current) generated and delivered to penis 90 may, for example, stimulate a controlled contraction of the penile muscles (e.g., cavernosal smooth muscles) thereof, thereby preventing muscle's atrophy and/or improving muscles performance.

In some embodiments, device 200 may be positioned at a predetermined distance 97 from a base 99 of penis 90 (e.g., as shown in FIG. 5E). Distance 97 may be predetermined based on a target treatment region of penis 90. In some embodiments, distance 97 may be varied (e.g., using reusable support 240) during a treatment procedure to apply the treatment (e.g., to deliver RF energy) to various regions along penis 90. In various embodiments, distance 97 may be continuously varied (e.g., using reusable support 240) during a treatment procedure to apply the treatment to a larger region of penis 90 and/or to avoid overheating of a specific region of penis 90 above a predetermined temperature threshold.

Figure 5F:
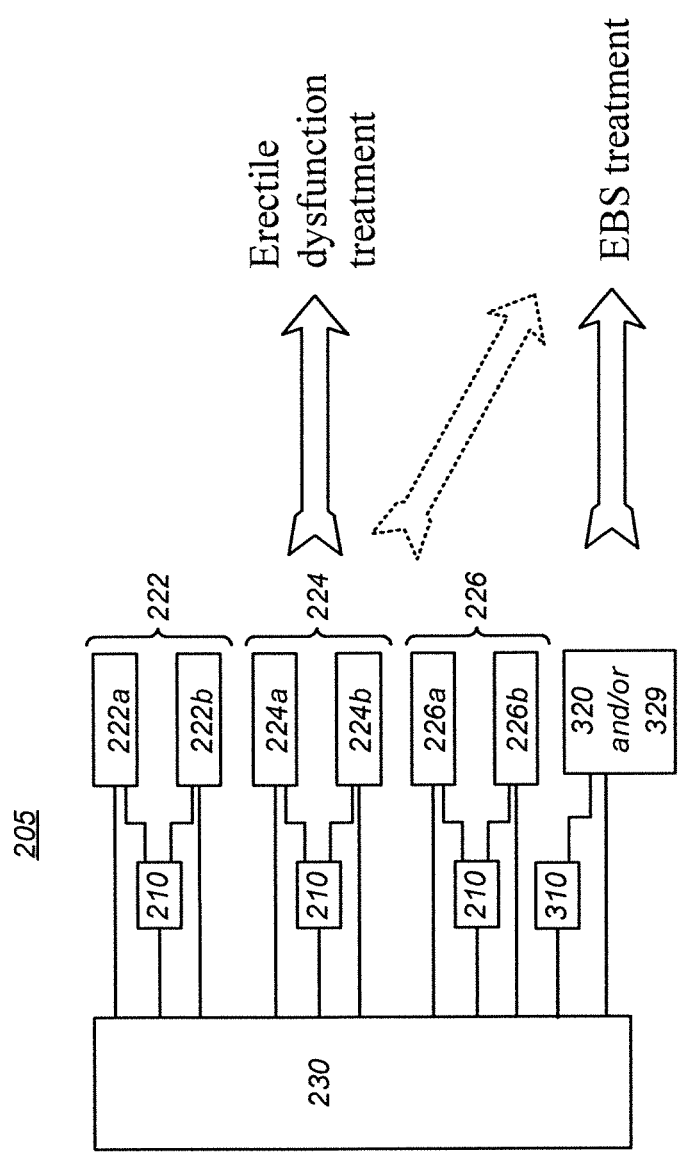
FIG. 5F is a high level schematic block diagram of electronic circuitry of the device for treating erectile dysfunction as well as providing erectile body stimulation (EBS) treatment by the erectile body stimulation (EBS) kit, according to some embodiments of the invention.

FIG. 5F is a high level schematic block diagram of electronic circuitry 205 of device 200 for treating erectile dysfunction as well as providing EBS treatment by EBS kit 400, according to some embodiments of the invention. Control circuitry 230 and/or electronic circuitry 205 may be further configured to control the EBS treatment in addition to controlling the erectile dysfunction treatment (see FIG. 3G), simultaneously, alternatingly and/or alternatively. RF electrode pairs 220 may be used for EBS treatment as well as for erectile dysfunction treatment (as indicated schematically be the broken arrow), and/or EBS treatment may be applied in no connection to RF electrode pairs 220. In some embodiments, control circuitry 230 may be configured to deliver RF energy between RF electrodes 320 of pad 300 and RF electrodes of RF electrode pairs 220 of device 200. For example, each RF electrode of RF electrodes 320 of pad 300 may be coupled to one of RF electrodes in one of RF electrode pairs 220 of device 200 and control circuitry 230 may be further configured to deliver RF energy between the coupled RF electrodes thereof.

In some embodiments, control circuitry 230 may be configured to apply RF energy to penis 90 between RF electrodes of RF electrode pairs 220 of device 200 (e.g., as described above with respect to FIGS. 3A-3G). In some embodiments, control circuitry 230 may be configured to apply RF energy to penis 90 between coupled RF electrodes 320 of pad 300 and RF electrodes of RF electrode pairs 220 of device 200 (e.g., as described above with respect to FIG. 5D).

In some embodiments, control circuitry 230 may be configured to apply RF energy and the predetermined electrical current to penis 90 according to a predetermined plan. For example, control circuitry 230 may be configured to apply RF energy to penis 90 between RF electrodes of RF electrode pairs 220 of device 200 (e.g., as described above with respect to FIGS. 3A-3G), or optionally via coupled RF electrodes 320 of pad 300 and RF electrodes of RF electrode pairs 220 of device 200 (e.g., as described above with respect to FIG. 5D), and to apply at predetermined time points (e.g., each 10-30 msec) the predetermined current pulse between electrode 329 of pad 300 and electrode 229 of device 200.

Certain embodiments comprise a system comprising: at least one radiofrequency (RF) generator 210 configured to generate RF energy, a reusable support 240, a disposable support 250 removably connectable to reusable support 240, disposable support 250 comprising a plurality of RF electrode pairs 220, each RF electrode in each RF electrode pair of plurality of RF electrode pairs 220 configured to contact a target penile surface 96 and connected to at least one RF generator of the at least one RF generator 210, wherein a removable connection between reusable support 240 and disposable support 250 is configured to enable delivery of the RF energy to each RF electrode in each RF electrode pair of plurality of RF electrode pairs 220, a control circuitry 230 connected to each RF electrode in each RF electrode pair of plurality of RF electrode pairs 220 and connected to at least one RF generator of the at least one RF generator 210, control circuitry 230 configured to switch among RF electrode pairs of plurality of RF electrode pairs 220 to apply the generated RF energy to penis 90 to thereby elevate a temperature of internal penile tissue above a predetermined temperature value while maintaining a penile surface 96 below a predetermined temperature threshold, and a pad 300 for erectile body (EBS) stimulation mechanically attachable to a perineum 98 of a patient and configured to electrically stimulate penile muscles by applying at predetermined time points predetermined electrical current pulses between at least one additional electrode 329 on pad 300 and at least one additional electrode 229 on disposable support 250.

FIG. 6 is a high level schematic flowchart illustrating a method 500 of erectile dysfunction treatment, according to some embodiments of the invention. Method 500 may be implemented by a device 200 and/or pad 300 disclosed above, or by any equivalent apparatus which implements at least some of the stages of method 500. Stages from method 500 may be also part of method 100 illustrated in FIG. 2 and stages from method 100 may be also part of method 500. Methods 500 and/or 100 may be implemented by any operable combination of the following stages, irrespective of their order.

Method 500 may comprise delivering radiofrequency (RF) energy to inner penile tissues of a penis of a patient (e.g., corpora cavernosa 91, tunica albuginea 94, penile septum 95, etc., as shown in FIG. 1A) via plurality of RF electrode pairs contacting a penile surface (stage 510).

In some embodiments, method 500 may comprise arranging the RF electrodes along a circumference of the penis such that each RF electrode in each of the RF electrode pairs of the plurality of RF electrode pairs is positioned at a substantially opposite side of the penis (e.g., as described above with respect to FIGS. 3A-3C) to provide an opposite RF electrodes arrangement (stage 520). In some embodiments, method 500 may comprise arranging the RF electrodes along a circumference of the penis such that RF electrodes in each RF electrode pair of the plurality of RF electrode pairs are positioned adjacent to each other (e.g., as described above with respect to FIGS. 3D-3E) to provide adjacent RF electrodes arrangement (stage 522).

In some embodiments, method 500 may comprise arranging the RF electrodes in multiple sets of RF electrode pairs (e.g., as shown above with respect to FIGS. 4C-4E), wherein the RF electrodes in each of the sets of RF electrode pairs are arranged along a circumference of the penis and wherein each of the sets of RF electrode pairs is positioned at different predetermined location along the penis (stage 523). In some embodiments, method 500 may comprise coupling RF electrodes from different sets of RF electrodes pairs to provide coupled RF electrode pairs, wherein the RF electrodes in each of the coupled RF electrode pairs are positioned at opposite portions of the penis with respect to each other to provide the opposite RF electrodes arrangement (e.g., as described above with respect to FIG. 4C; stage 524). In some embodiments, method 500 may comprise coupling RF electrodes from different sets of RF electrodes pairs to provide coupled RF electrode pairs, wherein the RF electrodes in each of the coupled RF electrode pairs are positioned at the same portion of the penis to provide the adjacent RF electrodes arrangement (e.g., as described above with respect to FIG. 4C; stage 525).

Method 500 may comprise operating the RF electrode pairs according to a predetermined operation pattern (stage 530). Method 500 may comprise designing the predetermined operation pattern to activate single RF electrode pair of the plurality of RF electrode pairs at a predetermined time point and during a predetermined time duration, while deactivating remaining RF electrode pairs of the plurality of RF electrode pairs (stage 532; e.g., as described above with respect to FIG. 3A and FIG. 3D). Method 500 may comprise designing the predetermined operation pattern to activate at least two RF electrode pairs of the plurality of RF electrode pairs at a predetermined time point and during a predetermined time duration, while deactivating at least one RF electrode pair of the plurality of RF electrode pairs (stage 534; e.g., as described above with respect to FIG. 3B and FIG. 3E). Method 500 may comprise isolating each RF electrode pair of the plurality of RF electrode pairs to prevent unintended current paths between RF electrodes of the operating RF electrode pairs and deactivated RF electrode pairs (stage 535; e.g., as described above with respect to FIGS. 3F and 3G).

In some embodiments, method 500 may comprise configuring the opposite RF electrodes arrangement to deliver RF energy to a target inner penile tissue to thereby elevate a temperature of the target tissue to a predetermined temperature value, while keeping the penile surface below a predetermined temperature threshold (stage 536; e.g., as described above with respect to FIGS. 3A-3C). In some embodiments, method 500 may comprise maintaining the temperature of the target inner penile tissue at the predetermined temperature value during a predetermined time duration to induce a desired treatment effect (stage 537; e.g., as described above with respect to FIG. 2). In some embodiments, method 500 may comprise configuring the adjacent RF electrodes arrangement to deliver RF energy to the penile surface and to thereby elevate a temperature of the penile surface to a predetermined temperature value without significantly effecting inner penile tissues (stage 538; e.g., as described above with respect to FIGS. 3D-3E).

Method 500 may comprise attaching at least one RF electrode and at least one additional electrode to a perineum of the patient (stage 540; e.g., as describe above with respect to FIGS. 5A-5F). Method 500 may comprise attaching at least one additional electrode to the penile surface (stage 542). In some embodiments, method 500 may comprise adapting the at least one additional electrode(s) to deliver a low frequency current (stage 543). In some embodiments, method 500 may comprise delivering RF energy to the penis between the RF electrodes contacting the perineum and RF electrodes of the RF electrode pairs contacting the penile surface (stage 544; e.g., as described above with respect to FIGS. 5D-5E). In some embodiments, method 500 may comprise delivering a predetermined electrical current between the at least one additional electrode contacting the perineum and the at least one additional electrode contacting the penile surface (stage 546; e.g., as described above with respect to FIGS. 5D-5E). In some embodiments, method 500 may comprise delivering RF energy to the penis between RF electrodes of the RF electrode pairs contacting the penile surface and applying at predetermined time points the predetermined current pulses between the at least one additional electrode contacting the perineum and the at least one additional electrode contacting the penile surface (stage 548; e.g., as described above with respect to FIGS. 5D-5E). In some embodiments, method 500 may comprise configuring the predetermined electrical current to stimulate penile muscles (e.g., cavernosal smooth muscles; stage 549).

In some embodiments, method 500 may comprise attaching a single RF electrode and a return plate to the penile surface and delivering RF energy to the penis between the single RF electrode and the return plate thereof to elevate a temperature of inner penile tissues or of the penile surface to a predetermined temperature value (stage 550).

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method of treating erectile dysfunction (ED), the method comprising:
    delivering energy, non-invasively, to a penile tissue comprising at least one of tunica albuginea and penile septum, wherein the delivered energy comprises a radiofrequency (RF) energy applied between at least two RF electrodes contacting an outer skin surface of a penis or between at least one RF electrode contacting the outer skin surface of the penis and a return plate, wherein the energy is delivered using a plurality of RF electrode pairs externally arranged along a circumference of the penis, wherein RF electrodes in each RF electrode pair of the plurality of RF electrode pairs contact the outer skin surface of the penis at a substantially opposite side of the penis with respect to each other,
    applying, at predetermined time points, predetermined electrical current pulses between at least one additional electrode contacting a perineum of a patient and at least one additional electrode contacting the outer skin surface of the penis, and
    controlling the delivered energy to initiate synthesis of collagen fibers in the penile tissue.

2. The method of claim 1, further comprising controlling the delivered energy to elevate a temperature of the penile tissue to a predetermined temperature value that causes initiation of the collagen fibers synthesis, while maintaining a temperature of an outer skin surface of a penis below a predetermined temperature threshold.

3. The method of claim 2, further comprising controlling the delivered energy to initiate at least one of alignment, remodeling and regeneration of collagen fibers or elastin fibers in the penile tissue.

4. The method of claim 2, wherein the energy is delivered from a penis's periphery inwards using multiple peripheral energy sources.

5. The method of claim 4, wherein the maintaining the temperature of the outer skin surface of the penis is carried out by switching energy delivering peripheral energy sources among the multiple energy delivering peripheral energy sources before reaching the predetermined temperature threshold.

6. The method of claim 2, wherein the predetermined temperature value is within a range between 42° C. and 52° C.

7. The method of claim 2, wherein the predetermined temperature threshold is within a range between 38° C. and 44° C.

8. The method of claim 1, further comprising controlling the delivered energy to treat a venous leak disease or venous leak mechanism.

9. The method of claim 1, further comprising delivering energy to at least one of corpora cavernosa and penile smooth muscle tissue.

10. The method of claim 9, further comprising controlling the delivered energy to at least one of increase oxygenation of endothelial cells, improve blood flow in the penis, initiate angiogenesis in the penis and initiate neovascularization in the penis.

11. The method of claim 1, further comprising operating the plurality of RF electrode pairs according to a predetermined operation pattern.

12. The method of claim 11, further comprising determining the operation pattern to drive the RF energy through the penile tissue while switching among RF electrode pairs of the plurality of RF electrode pairs to thereby elevate a temperature of the penile tissue above a predetermined temperature value while maintaining the outer skin surface of the penis below a predetermined temperature threshold.

13. The method of claim 1, further comprising controlling the predetermined electrical current pulses to stimulate penile muscles.

14. The method of claim 1, wherein the delivered energy comprises RF conduction.

15. The method of claim 1, wherein the delivered energy further comprises at least one of: ultrasound (US) energy, infrared (IR) energy and photonic energy.

16. A method of a non-invasive erectile dysfunction the method comprising:
    delivering radiofrequency (RF) energy to a penile tissue comprising at least one of tunica albuginea and penile septum via a plurality of RF electrode pairs externally arranged along a circumference of a penis, wherein RF electrodes in each RF electrode pair of the plurality of RF electrode pairs contact an outer skin surface of the penis at a substantially opposite side of the penis with respect to each other,
    operating the plurality of RF electrode pairs according to an operation pattern predetermined to drive the RF energy through the penile tissue while switching among RF electrode pairs of the plurality of RF electrode pairs to elevate a temperature of the penile tissue above a predetermined temperature value to thereby initiate synthesis of collagen fibers in the penile tissue, while maintaining the outer skin surface of the penis below a predetermined temperature threshold, and
    applying, at predetermined time points, predetermined electrical current pulses between at least one additional electrode contacting a perineum of a patient and at least one additional electrode contacting the outer skin surface of the penis.

17. The method of claim 16, further comprising applying, at predetermined time points, predetermined electrical current pulses between at least one additional electrode contacting a perineum of a patient and at least one additional electrode contacting the outer skin surface of the penis, wherein the predetermined electrical current pulses are arranged to stimulate penile muscles.

18. A method of a non-invasive erectile dysfunction (ED) treatment using radiofrequency (RF) energy delivered, externally, to a penis, the method comprising:
   securely attaching a flexible sleeve to the penis, the sleeve having a plurality of RF electrodes configured to deliver the RF energy alternatingly, to heat internal penile tissue above a predetermined temperature value while maintaining the outer skin surface of the penis below a predetermined temperature threshold, and
   operating the RF electrodes while the secure attachment of the flexible sleeve to the penis is maintained.

19. The method of claim 18, wherein the internal penile tissue comprises at least a tunica albuginea and/or a penile septum of the penis, and wherein the alternating RF energy delivery comprises switching the RF electrodes to avoid overheating outer skin while maintaining RE energy delivery to the internal penile tissue.

20. The method of claim 16, further comprising controlling the delivered energy to: (i) elevate a temperature of the penile tissue to a predetermined temperature value that causes initiation of the collagen fibers synthesis, while maintaining a temperature of an outer skin surface of a penis below a predetermined temperature threshold, (ii) treat a venous leak disease or venous leak mechanism, (iii) reach the corpora cavernosa and/or the penile smooth muscle tissue, and/or (iv) stimulate penile muscles.

21. The method of claim 18, further comprising controlling the delivered energy to: (i) elevate a temperature of the penile tissue to a predetermined temperature value that causes initiation of the collagen fibers synthesis, while maintaining a temperature of an outer skin surface of a penis below a predetermined temperature threshold, (ii) treat a venous leak disease or venous leak mechanism, (iii) reach the corpora cavernosa and/or the penile smooth muscle tissue, and/or (iv) stimulate penile muscles.

* * * * *

UNITED STATES PATENT AND TRADEMARK OFFICE
CERTIFICATE OF CORRECTION

PATENT NO. : 10,729,904 B2
APPLICATION NO. : 15/878423
DATED : August 4, 2020
INVENTOR(S) : Lischinsky Page 1 of 1

It is certified that error appears in the above-identified patent and that said Letters Patent is hereby corrected as shown below:

In the Claims

In Column 18, Claim 16, Line 40, delete "dysfunction" and insert -- dysfunction treatment, --, therefor.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*